US011801344B2

(12) United States Patent
Cardinali et al.

(10) Patent No.: US 11,801,344 B2
(45) Date of Patent: Oct. 31, 2023

(54) BLOOD GLUCOSE RATE OF CHANGE MODULATION OF MEAL AND CORRECTION INSULIN BOLUS QUANTITY

(71) Applicant: Insulet Corporation, Acton, MA (US)

(72) Inventors: Steven Cardinali, Tewksbury, MA (US); Joon Bok Lee, Acton, MA (US); Jason O'Connor, Acton, MA (US); Yibin Zheng, Hartland, WI (US)

(73) Assignee: INSULET CORPORATION, Acton, MA (US)

( * ) Notice: Subject to any disclaimer, the term of this patent is extended or adjusted under 35 U.S.C. 154(b) by 430 days.

(21) Appl. No.: 16/570,125

(22) Filed: Sep. 13, 2019

(65) Prior Publication Data

US 2021/0077719 A1    Mar. 18, 2021

(51) Int. Cl.
*A61M 5/172*    (2006.01)
*G16H 20/17*    (2018.01)
(Continued)

(52) U.S. Cl.
CPC ........ *A61M 5/1723* (2013.01); *A61B 5/14532* (2013.01); *G16H 10/60* (2018.01);
(Continued)

(58) Field of Classification Search
CPC ........ G16H 20/17; G16H 40/63; G16H 50/20; G16H 50/30; G16H 40/60; G16H 20/10;
(Continued)

(56) References Cited

U.S. PATENT DOCUMENTS 303,013 A    8/1884  Horton
2,797,149 A    6/1957  Skeggs
(Continued)

FOREIGN PATENT DOCUMENTS

AU    2015200834 A1    3/2015
AU    2015301146 A1    3/2017
(Continued)

OTHER PUBLICATIONS

US 5,954,699 A, 09/1999, Jost et al. (withdrawn)
(Continued)

*Primary Examiner* — Carrie R Dorna
*Assistant Examiner* — Karen E Toth
(74) *Attorney, Agent, or Firm* — GOODWIN PROCTER LLP

(57) ABSTRACT

Disclosed are a system, methods and computer-readable medium products that provide bolus dosage calculations by a control algorithm-based drug delivery system that provides automatic delivery of a drug, such as insulin or the like, based on sensor input. Blood glucose measurement values may be received at regular time intervals from a sensor. Using the blood glucose measurements, the control algorithm may perform various calculations and determinations to provide an appropriate bolus dosage. The appropriate bolus dosage may be used to respond to a trend in a trajectory of blood glucose measurements. In addition, a bolus dosage may also be determined by the disclosed device, system, method and/or computer-readable medium product in response to an indication that a user consumed a meal.

18 Claims, 8 Drawing Sheets

(51) Int. Cl.
*G16H 10/60* (2018.01)
*A61B 5/145* (2006.01)
*G16H 15/00* (2018.01)
*A61B 5/00* (2006.01)
*A61M 5/142* (2006.01)

(52) U.S. Cl.
CPC ............ *G16H 20/17* (2018.01); *A61B 5/4839* (2013.01); *A61B 5/683* (2013.01); *A61M 5/14244* (2013.01); *A61M 2005/14208* (2013.01); *A61M 2005/1726* (2013.01); *A61M 2205/52* (2013.01); *A61M 2230/201* (2013.01); *G16H 15/00* (2018.01)

(58) Field of Classification Search
CPC .......... A61M 5/1723; A61M 2230/201; A61M 2005/14208; A61M 2230/005; A61M 2005/1726; A61B 5/14532; A61B 5/4839; A61B 5/7275
See application file for complete search history.

(56) References Cited

U.S. PATENT DOCUMENTS

| | | |
|---|---|---|
| 3,631,847 A | 1/1972 | Hobbs |
| 3,634,039 A | 1/1972 | Brondy |
| 3,812,843 A | 5/1974 | Wootten et al. |
| 3,841,328 A | 10/1974 | Jensen |
| 3,963,380 A | 6/1976 | Thomas, Jr. et al. |
| 4,055,175 A | 10/1977 | Clemens et al. |
| 4,146,029 A | 3/1979 | Ellinwood, Jr. |
| 4,151,845 A | 5/1979 | Clemens |
| 4,245,634 A | 1/1981 | Albisser et al. |
| 4,368,980 A | 1/1983 | Aldred et al. |
| 4,373,527 A | 2/1983 | Fischell |
| 4,403,984 A | 9/1983 | Ash et al. |
| 4,464,170 A | 8/1984 | Clemens et al. |
| 4,469,481 A | 9/1984 | Kobayashi |
| 4,475,901 A | 10/1984 | Kraegen et al. |
| 4,526,568 A | 7/1985 | Clemens et al. |
| 4,526,569 A | 7/1985 | Bernardi |
| 4,529,401 A | 7/1985 | Leslie et al. |
| 4,559,033 A | 12/1985 | Stephen et al. |
| 4,559,037 A | 12/1985 | Franetzki et al. |
| 4,573,968 A | 3/1986 | Parker |
| 4,624,661 A | 11/1986 | Arimond |
| 4,633,878 A | 1/1987 | Bombardieri |
| 4,657,529 A | 4/1987 | Prince et al. |
| 4,685,903 A | 8/1987 | Cable et al. |
| 4,731,726 A | 3/1988 | Allen, III |
| 4,743,243 A | 5/1988 | Vaillancourt |
| 4,755,173 A | 7/1988 | Konopka et al. |
| 4,781,688 A | 11/1988 | Thoma et al. |
| 4,781,693 A | 11/1988 | Martinez et al. |
| 4,808,161 A | 2/1989 | Kamen |
| 4,854,170 A | 8/1989 | Brimhall et al. |
| 4,886,499 A | 12/1989 | Cirelli et al. |
| 4,900,292 A | 2/1990 | Berry et al. |
| 4,919,596 A | 4/1990 | Slate et al. |
| 4,925,444 A | 5/1990 | Orkin et al. |
| 4,940,527 A | 7/1990 | Kazlauskas et al. |
| 4,975,581 A | 12/1990 | Robinson et al. |
| 4,976,720 A | 12/1990 | Machold et al. |
| 4,981,140 A | 1/1991 | Wyatt |
| 4,994,047 A | 2/1991 | Walker et al. |
| 5,007,286 A | 4/1991 | Malcolm et al. |
| 5,097,834 A | 3/1992 | Skrabal |
| 5,102,406 A | 4/1992 | Arnold |
| 5,109,850 A | 5/1992 | Blanco et al. |
| 5,125,415 A | 6/1992 | Bell |
| 5,134,079 A | 7/1992 | Cusack et al. |
| 5,153,827 A | 10/1992 | Coutre et al. |
| 5,165,406 A | 11/1992 | Wong |
| 5,176,662 A | 1/1993 | Bartholomew et al. |
| 5,178,609 A | 1/1993 | Ishikawa |
| 5,207,642 A | 5/1993 | Orkin et al. |
| 5,232,439 A | 8/1993 | Campbell et al. |
| 5,237,993 A | 8/1993 | Skrabal |
| 5,244,463 A | 9/1993 | Cordner, Jr. et al. |
| 5,257,980 A | 11/1993 | Van Antwerp et al. |
| 5,273,517 A | 12/1993 | Barone et al. |
| 5,281,808 A | 1/1994 | Kunkel |
| 5,299,571 A | 4/1994 | Mastrototaro |
| 5,308,982 A | 5/1994 | Ivaldi et al. |
| 5,342,298 A | 8/1994 | Michaels et al. |
| 5,377,674 A | 1/1995 | Kuestner |
| 5,380,665 A | 1/1995 | Cusack et al. |
| 5,385,539 A | 1/1995 | Maynard |
| 5,389,078 A | 2/1995 | Zalesky |
| 5,411,889 A | 5/1995 | Hoots et al. |
| 5,421,812 A | 6/1995 | Langley et al. |
| 5,468,727 A | 11/1995 | Phillips et al. |
| 5,505,709 A | 4/1996 | Funderburk et al. |
| 5,505,828 A | 4/1996 | Wong et al. |
| 5,507,288 A | 4/1996 | Bocker et al. |
| 5,533,389 A | 7/1996 | Kamen et al. |
| 5,558,640 A | 9/1996 | Pfeiler et al. |
| 5,569,186 A | 10/1996 | Lord et al. |
| 5,584,813 A | 12/1996 | Livingston et al. |
| 5,609,572 A | 3/1997 | Lang |
| 5,665,065 A | 9/1997 | Colman et al. |
| 5,678,539 A | 10/1997 | Schubert et al. |
| 5,685,844 A | 11/1997 | Marttila |
| 5,685,859 A | 11/1997 | Kornerup |
| 5,693,018 A | 12/1997 | Kriesel et al. |
| 5,697,899 A | 12/1997 | Hillman et al. |
| 5,700,695 A | 12/1997 | Yassinzadeh et al. |
| 5,703,364 A | 12/1997 | Rosenthal |
| 5,714,123 A | 2/1998 | Sohrab |
| 5,716,343 A | 2/1998 | Kriesel et al. |
| 5,722,397 A | 3/1998 | Eppstein |
| 5,741,228 A | 4/1998 | Lambrecht et al. |
| 5,746,217 A | 5/1998 | Erickson et al. |
| 5,755,682 A | 5/1998 | Knudson et al. |
| 5,758,643 A | 6/1998 | Wong et al. |
| 5,800,405 A | 9/1998 | McPhee |
| 5,800,420 A | 9/1998 | Gross et al. |
| 5,801,057 A | 9/1998 | Smart et al. |
| 5,804,048 A | 9/1998 | Wong et al. |
| 5,817,007 A | 10/1998 | Fodgaard et al. |
| 5,820,622 A | 10/1998 | Gross et al. |
| 5,823,951 A | 10/1998 | Messerschmidt |
| 5,840,020 A | 11/1998 | Heinonen et al. |
| 5,848,991 A | 12/1998 | Gross et al. |
| 5,851,197 A | 12/1998 | Marano et al. |
| 5,858,005 A | 1/1999 | Kriesel |
| 5,865,806 A | 2/1999 | Howell |
| 5,871,470 A | 2/1999 | McWha |
| 5,879,310 A | 3/1999 | Sopp et al. |
| 5,902,253 A | 5/1999 | Pfeiffer et al. |
| 5,931,814 A | 8/1999 | Alex et al. |
| 5,932,175 A | 8/1999 | Knute et al. |
| 5,935,099 A | 8/1999 | Peterson et al. |
| 5,947,911 A | 9/1999 | Wong et al. |
| 5,971,941 A | 10/1999 | Simons et al. |
| 5,993,423 A | 11/1999 | Choi |
| 5,997,501 A | 12/1999 | Gross et al. |
| 6,017,318 A | 1/2000 | Gauthier et al. |
| 6,024,539 A | 2/2000 | Blomquist |
| 6,032,059 A | 2/2000 | Henning et al. |
| 6,036,924 A | 3/2000 | Simons et al. |
| 6,040,578 A | 3/2000 | Malin et al. |
| 6,049,727 A | 4/2000 | Grothall |
| 6,050,978 A | 4/2000 | Orr et al. |
| 6,058,934 A | 5/2000 | Sullivan |
| 6,066,103 A | 5/2000 | Duchon et al. |
| 6,071,292 A | 6/2000 | Makower et al. |
| 6,072,180 A | 6/2000 | Kramer et al. |
| 6,077,055 A | 6/2000 | Vilks |
| 6,090,092 A | 7/2000 | Fowles et al. |
| 6,101,406 A | 8/2000 | Hacker et al. |
| 6,102,872 A | 8/2000 | Doneen et al. |
| 6,115,673 A | 9/2000 | Malin et al. |
| 6,123,827 A | 9/2000 | Wong et al. |

(56) References Cited

U.S. PATENT DOCUMENTS

| | | |
|---|---|---|
| 6,124,134 A | 9/2000 | Stark |
| 6,126,637 A | 10/2000 | Kriesel et al. |
| 6,128,519 A | 10/2000 | Say |
| 6,142,939 A | 11/2000 | Eppstein et al. |
| 6,143,164 A | 11/2000 | Heller et al. |
| 6,157,041 A | 12/2000 | Thomas et al. |
| 6,161,028 A | 12/2000 | Braig et al. |
| 6,162,639 A | 12/2000 | Douglas |
| 6,196,046 B1 | 3/2001 | Braig et al. |
| 6,200,287 B1 | 3/2001 | Keller et al. |
| 6,200,338 B1 | 3/2001 | Solomon et al. |
| 6,214,629 B1 | 4/2001 | Freitag et al. |
| 6,226,082 B1 | 5/2001 | Roe |
| 6,244,776 B1 | 6/2001 | Wiley |
| 6,261,065 B1 | 7/2001 | Nayak et al. |
| 6,262,798 B1 | 7/2001 | Shepherd et al. |
| 6,270,455 B1 | 8/2001 | Brown |
| 6,271,045 B1 | 8/2001 | Douglas et al. |
| 6,280,381 B1 | 8/2001 | Malin et al. |
| 6,285,448 B1 | 9/2001 | Kuenstner |
| 6,309,370 B1 | 10/2001 | Haim et al. |
| 6,312,888 B1 | 11/2001 | Wong et al. |
| 6,334,851 B1 | 1/2002 | Hayes et al. |
| 6,375,627 B1 | 4/2002 | Mauze et al. |
| 6,379,301 B1 | 4/2002 | Worthington et al. |
| 6,402,689 B1 | 6/2002 | Scarantino et al. |
| 6,470,279 B1 | 10/2002 | Samsoondar |
| 6,475,196 B1 | 11/2002 | Vachon |
| 6,477,901 B1 | 11/2002 | Tadigadapa et al. |
| 6,484,044 B1 | 11/2002 | Lilienfeld-Toal |
| 6,491,656 B1 | 12/2002 | Morris |
| 6,512,937 B2 | 1/2003 | Blank et al. |
| 6,525,509 B1 | 2/2003 | Petersson et al. |
| 6,528,809 B1 | 3/2003 | Thomas et al. |
| 6,540,672 B1 | 4/2003 | Simonsen et al. |
| 6,544,212 B2 | 4/2003 | Galley et al. |
| 6,546,268 B1 | 4/2003 | Ishikawa et al. |
| 6,546,269 B1 | 4/2003 | Kurnik |
| 6,553,841 B1 | 4/2003 | Blouch |
| 6,554,798 B1 | 4/2003 | Mann et al. |
| 6,556,850 B1 | 4/2003 | Braig et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,562,014 B2 | 5/2003 | Lin et al. |
| 6,569,125 B2 | 5/2003 | Jepson et al. |
| 6,572,542 B1 | 6/2003 | Houben et al. |
| 6,572,545 B2 | 6/2003 | Knobbe et al. |
| 6,574,490 B2 | 6/2003 | Abbink et al. |
| 6,575,905 B2 | 6/2003 | Knobbe et al. |
| 6,580,934 B1 | 6/2003 | Braig et al. |
| 6,618,603 B2 | 9/2003 | Varalli et al. |
| 6,633,772 B2 | 10/2003 | Ford et al. |
| 6,645,142 B2 | 11/2003 | Braig et al. |
| 6,653,091 B1 | 11/2003 | Dunn et al. |
| 6,662,030 B2 | 12/2003 | Khalil et al. |
| 6,669,663 B1 | 12/2003 | Thompson |
| 6,678,542 B2 | 1/2004 | Braig et al. |
| 6,699,221 B2 | 3/2004 | Vaillancourt |
| 6,718,189 B2 | 4/2004 | Rohrscheib et al. |
| 6,721,582 B2 | 4/2004 | Trepagnier et al. |
| 6,728,560 B2 | 4/2004 | Kollias et al. |
| 6,740,059 B2 | 5/2004 | Flaherty |
| 6,740,072 B2 | 5/2004 | Starkweather et al. |
| 6,751,490 B2 | 6/2004 | Esenaliev et al. |
| 6,758,835 B2 | 7/2004 | Close et al. |
| 6,780,156 B2 | 8/2004 | Haueter et al. |
| 6,810,290 B2 | 10/2004 | Lebel et al. |
| 6,837,858 B2 | 1/2005 | Cunningham et al. |
| 6,837,988 B2 | 1/2005 | Leong et al. |
| 6,846,288 B2 | 1/2005 | Nagar et al. |
| 6,862,534 B2 | 3/2005 | Sterling et al. |
| 6,865,408 B1 | 3/2005 | Abbink et al. |
| 6,890,291 B2 | 5/2005 | Robinson et al. |
| 6,936,029 B2 | 8/2005 | Mann et al. |
| 6,949,081 B1 | 9/2005 | Chance |
| 6,958,809 B2 | 10/2005 | Sterling et al. |
| 6,989,891 B2 | 1/2006 | Braig et al. |
| 6,990,366 B2 | 1/2006 | Say et al. |
| 7,008,404 B2 | 3/2006 | Nakajima |
| 7,009,180 B2 | 3/2006 | Sterling et al. |
| 7,016,713 B2 | 3/2006 | Gardner et al. |
| 7,018,360 B2 | 3/2006 | Flaherty et al. |
| 7,025,743 B2 | 4/2006 | Mann et al. |
| 7,025,744 B2 | 4/2006 | Utterberg et al. |
| 7,027,848 B2 | 4/2006 | Robinson et al. |
| 7,043,288 B2 | 5/2006 | Davis, III et al. |
| 7,060,059 B2 | 6/2006 | Keith et al. |
| 7,061,593 B2 | 6/2006 | Braig et al. |
| 7,096,124 B2 | 8/2006 | Sterling et al. |
| 7,115,205 B2 | 10/2006 | Robinson et al. |
| 7,128,727 B2 | 10/2006 | Flaherty et al. |
| 7,139,593 B2 | 11/2006 | Kavak et al. |
| 7,139,598 B2 | 11/2006 | Hull et al. |
| 7,144,384 B2 | 12/2006 | Gorman et al. |
| 7,171,252 B1 | 1/2007 | Scarantino et al. |
| 7,190,988 B2 | 3/2007 | Say et al. |
| 7,204,823 B2 | 4/2007 | Estes et al. |
| 7,248,912 B2 | 7/2007 | Gough et al. |
| 7,267,665 B2 | 9/2007 | Steil et al. |
| 7,271,912 B2 | 9/2007 | Sterling et al. |
| 7,278,983 B2 | 10/2007 | Ireland et al. |
| 7,291,107 B2 | 11/2007 | Hellwig et al. |
| 7,291,497 B2 | 11/2007 | Holmes et al. |
| 7,303,549 B2 | 12/2007 | Flaherty et al. |
| 7,303,622 B2 | 12/2007 | Loch et al. |
| 7,303,922 B2 | 12/2007 | Jeng et al. |
| 7,354,420 B2 | 4/2008 | Steil et al. |
| 7,388,202 B2 | 6/2008 | Sterling et al. |
| 7,402,153 B2 | 7/2008 | Steil et al. |
| 7,404,796 B2 | 7/2008 | Ginsberg |
| 7,429,255 B2 | 9/2008 | Thompson |
| 7,460,130 B2 | 12/2008 | Salganicoff |
| 7,481,787 B2 | 1/2009 | Gable et al. |
| 7,491,187 B2 | 2/2009 | Van Den Berghe et al. |
| 7,500,949 B2 | 3/2009 | Gottlieb et al. |
| 7,509,156 B2 | 3/2009 | Flanders |
| 7,547,281 B2 | 6/2009 | Hayes et al. |
| 7,569,030 B2 | 8/2009 | Lebel et al. |
| 7,608,042 B2 | 10/2009 | Goldberger et al. |
| 7,651,845 B2 | 1/2010 | Doyle, III et al. |
| 7,680,529 B2 | 3/2010 | Kroll |
| 7,734,323 B2 | 6/2010 | Blomquist et al. |
| 7,766,829 B2 | 8/2010 | Sloan et al. |
| 7,785,258 B2 | 8/2010 | Braig et al. |
| 7,806,854 B2 | 10/2010 | Damiano et al. |
| 7,806,886 B2 | 10/2010 | Kanderian, Jr. et al. |
| 7,918,825 B2 | 4/2011 | OConnor et al. |
| 7,946,985 B2 | 5/2011 | Mastrototaro et al. |
| 7,972,296 B2 | 7/2011 | Braig et al. |
| 8,221,345 B2 | 7/2012 | Blomquist |
| 8,251,907 B2 | 8/2012 | Sterling et al. |
| 8,449,524 B2 | 5/2013 | Braig et al. |
| 8,452,359 B2 | 5/2013 | Rebec et al. |
| 8,454,576 B2 | 6/2013 | Mastrototaro et al. |
| 8,467,980 B2 | 6/2013 | Campbell et al. |
| 8,478,557 B2 | 7/2013 | Hayter et al. |
| 8,547,239 B2 | 10/2013 | Peatfield et al. |
| 8,597,274 B2 | 12/2013 | Sloan et al. |
| 8,622,988 B2 | 1/2014 | Hayter |
| 8,810,394 B2 | 8/2014 | Kalpin |
| 9,061,097 B2 | 6/2015 | Holt et al. |
| 9,171,343 B1 | 10/2015 | Fischell et al. |
| 9,233,204 B2 | 1/2016 | Booth et al. |
| 9,486,571 B2 | 11/2016 | Rosinko |
| 9,579,456 B2 | 2/2017 | Budiman et al. |
| 9,743,224 B2 | 8/2017 | San Vicente et al. |
| 9,907,515 B2 | 3/2018 | Doyle, III et al. |
| 9,980,140 B1 | 5/2018 | Spencer et al. |
| 9,984,773 B2 | 5/2018 | Gondhalekar et al. |
| 10,248,839 B2 | 4/2019 | Levy et al. |
| 10,335,464 B1 | 7/2019 | Michelich et al. |
| 10,583,250 B2 | 3/2020 | Mazlish et al. |

(56) References Cited

U.S. PATENT DOCUMENTS

| | | |
|---|---|---|
| 10,737,024 B2 | 8/2020 | Schmid |
| 10,987,468 B2 | 4/2021 | Mazlish et al. |
| 11,197,964 B2 | 12/2021 | Sjolund et al. |
| 11,260,169 B2 | 3/2022 | Estes |
| 2001/0021803 A1 | 9/2001 | Blank et al. |
| 2001/0034023 A1 | 10/2001 | Stanton, Jr. et al. |
| 2001/0034502 A1 | 10/2001 | Moberg et al. |
| 2001/0051377 A1 | 12/2001 | Hammer et al. |
| 2001/0053895 A1 | 12/2001 | Vaillancourt |
| 2002/0010401 A1 | 1/2002 | Bushmakin et al. |
| 2002/0010423 A1 | 1/2002 | Gross et al. |
| 2002/0016568 A1 | 2/2002 | Lebel et al. |
| 2002/0040208 A1 | 4/2002 | Flaherty et al. |
| 2002/0123740 A1 | 9/2002 | Flaherty et al. |
| 2002/0128543 A1 | 9/2002 | Leonhardt |
| 2002/0147423 A1 | 10/2002 | Burbank et al. |
| 2002/0155425 A1 | 10/2002 | Han et al. |
| 2002/0161288 A1 | 10/2002 | Shin et al. |
| 2003/0023148 A1 | 1/2003 | Lorenz et al. |
| 2003/0050621 A1 | 3/2003 | Lebel et al. |
| 2003/0060692 A1 | 3/2003 | Ruchti et al. |
| 2003/0086074 A1 | 5/2003 | Braig et al. |
| 2003/0086075 A1 | 5/2003 | Braig et al. |
| 2003/0090649 A1 | 5/2003 | Sterling et al. |
| 2003/0100040 A1 | 5/2003 | Bonnecaze et al. |
| 2003/0130616 A1 | 7/2003 | Steil et al. |
| 2003/0135388 A1 | 7/2003 | Martucci et al. |
| 2003/0144582 A1 | 7/2003 | Cohen et al. |
| 2003/0163097 A1 | 8/2003 | Fleury et al. |
| 2003/0195404 A1 | 10/2003 | Knobbe et al. |
| 2003/0208113 A1 | 11/2003 | Mault et al. |
| 2003/0208154 A1 | 11/2003 | Close et al. |
| 2003/0212379 A1 | 11/2003 | Bylund et al. |
| 2003/0216627 A1 | 11/2003 | Lorenz et al. |
| 2003/0220605 A1 | 11/2003 | Bowman, Jr. et al. |
| 2004/0010207 A1 | 1/2004 | Flaherty et al. |
| 2004/0034295 A1 | 2/2004 | Salganicoff |
| 2004/0045879 A1 | 3/2004 | Shults et al. |
| 2004/0051368 A1 | 3/2004 | Caputo et al. |
| 2004/0064259 A1 | 4/2004 | Haaland et al. |
| 2004/0097796 A1 | 5/2004 | Berman et al. |
| 2004/0116847 A1 | 6/2004 | Wall |
| 2004/0122353 A1 | 6/2004 | Shahmirian et al. |
| 2004/0133166 A1 | 7/2004 | Moberg et al. |
| 2004/0147034 A1 | 7/2004 | Gore et al. |
| 2004/0171983 A1 | 9/2004 | Sparks et al. |
| 2004/0203357 A1 | 10/2004 | Nassimi |
| 2004/0204868 A1 | 10/2004 | Maynard et al. |
| 2004/0215492 A1 | 10/2004 | Choi |
| 2004/0220517 A1 | 11/2004 | Starkweather et al. |
| 2004/0241736 A1 | 12/2004 | Hendee et al. |
| 2004/0249308 A1 | 12/2004 | Forssell |
| 2005/0003470 A1 | 1/2005 | Nelson et al. |
| 2005/0020980 A1 | 1/2005 | Inoue et al. |
| 2005/0022274 A1 | 1/2005 | Campbell et al. |
| 2005/0033148 A1 | 2/2005 | Haueter et al. |
| 2005/0049179 A1 | 3/2005 | Davidson et al. |
| 2005/0065464 A1 | 3/2005 | Talbot et al. |
| 2005/0065465 A1 | 3/2005 | Lebel et al. |
| 2005/0075624 A1 | 4/2005 | Miesel |
| 2005/0105095 A1 | 5/2005 | Pesach et al. |
| 2005/0137573 A1 | 6/2005 | McLaughlin |
| 2005/0171503 A1 | 8/2005 | Van Den Berghe et al. |
| 2005/0182306 A1 | 8/2005 | Sloan |
| 2005/0192494 A1 | 9/2005 | Ginsberg |
| 2005/0192557 A1 | 9/2005 | Brauker et al. |
| 2005/0197621 A1 | 9/2005 | Poulsen et al. |
| 2005/0203360 A1 | 9/2005 | Brauker et al. |
| 2005/0203461 A1 | 9/2005 | Flaherty et al. |
| 2005/0238507 A1 | 10/2005 | Dilanni et al. |
| 2005/0261660 A1 | 11/2005 | Choi |
| 2005/0272640 A1 | 12/2005 | Doyle et al. |
| 2005/0277912 A1 | 12/2005 | John |
| 2006/0009727 A1 | 1/2006 | OMahony et al. |
| 2006/0079809 A1 | 4/2006 | Goldberger et al. |
| 2006/0100494 A1 | 5/2006 | Kroll |
| 2006/0134323 A1 | 6/2006 | OBrien |
| 2006/0167350 A1 | 7/2006 | Monfre et al. |
| 2006/0173406 A1 | 8/2006 | Hayes et al. |
| 2006/0189925 A1 | 8/2006 | Gable et al. |
| 2006/0189926 A1 | 8/2006 | Hall et al. |
| 2006/0197015 A1 | 9/2006 | Sterling et al. |
| 2006/0200070 A1 | 9/2006 | Callicoat et al. |
| 2006/0204535 A1 | 9/2006 | Johnson |
| 2006/0229531 A1 | 10/2006 | Goldberger et al. |
| 2006/0253085 A1 | 11/2006 | Geismar et al. |
| 2006/0264895 A1 | 11/2006 | Flanders |
| 2006/0270983 A1 | 11/2006 | Lord et al. |
| 2006/0276771 A1 | 12/2006 | Galley et al. |
| 2006/0282290 A1 | 12/2006 | Flaherty et al. |
| 2007/0016127 A1 | 1/2007 | Staib et al. |
| 2007/0060796 A1 | 3/2007 | Kim |
| 2007/0060869 A1 | 3/2007 | Tolle et al. |
| 2007/0060872 A1 | 3/2007 | Hall et al. |
| 2007/0083160 A1 | 4/2007 | Hall et al. |
| 2007/0106135 A1 | 5/2007 | Sloan et al. |
| 2007/0116601 A1 | 5/2007 | Patton |
| 2007/0118405 A1 | 5/2007 | Campbell et al. |
| 2007/0129690 A1 | 6/2007 | Rosenblatt et al. |
| 2007/0142720 A1 | 6/2007 | Ridder et al. |
| 2007/0173761 A1 | 7/2007 | Kanderian et al. |
| 2007/0173974 A1 | 7/2007 | Lin |
| 2007/0179352 A1 | 8/2007 | Randlov et al. |
| 2007/0191716 A1 | 8/2007 | Goldberger et al. |
| 2007/0197163 A1 | 8/2007 | Robertson |
| 2007/0225675 A1 | 9/2007 | Robinson et al. |
| 2007/0244381 A1 | 10/2007 | Robinson et al. |
| 2007/0249007 A1 | 10/2007 | Rosero |
| 2007/0264707 A1 | 11/2007 | Liederman et al. |
| 2007/0282269 A1 | 12/2007 | Carter et al. |
| 2007/0287985 A1 | 12/2007 | Estes et al. |
| 2007/0293843 A1 | 12/2007 | Ireland et al. |
| 2008/0033272 A1 | 2/2008 | Gough et al. |
| 2008/0051764 A1 | 2/2008 | Dent et al. |
| 2008/0058625 A1 | 3/2008 | McGarraugh et al. |
| 2008/0065050 A1 | 3/2008 | Sparks et al. |
| 2008/0071157 A1 | 3/2008 | McGarraugh et al. |
| 2008/0071158 A1 | 3/2008 | McGarraugh et al. |
| 2008/0078400 A1 | 4/2008 | Martens et al. |
| 2008/0097289 A1 | 4/2008 | Steil et al. |
| 2008/0132880 A1 | 6/2008 | Buchman |
| 2008/0161664 A1 | 7/2008 | Mastrototaro et al. |
| 2008/0172026 A1 | 7/2008 | Blomquist |
| 2008/0177165 A1 | 7/2008 | Blomquist et al. |
| 2008/0188796 A1 | 8/2008 | Steil et al. |
| 2008/0200838 A1 | 8/2008 | Goldberger et al. |
| 2008/0206067 A1 | 8/2008 | De Corral et al. |
| 2008/0208113 A1 | 8/2008 | Damiano et al. |
| 2008/0214919 A1 | 9/2008 | Harmon et al. |
| 2008/0228056 A1 | 9/2008 | Blomquist et al. |
| 2008/0249386 A1 | 10/2008 | Besterman et al. |
| 2008/0269585 A1 | 10/2008 | Ginsberg |
| 2008/0269714 A1 | 10/2008 | Mastrototaro et al. |
| 2008/0269723 A1 | 10/2008 | Mastrototaro et al. |
| 2008/0287906 A1 | 11/2008 | Burkholz et al. |
| 2009/0006061 A1 | 1/2009 | Thukral et al. |
| 2009/0018406 A1 | 1/2009 | Yodfat et al. |
| 2009/0030398 A1 | 1/2009 | Yodfat et al. |
| 2009/0036753 A1 | 2/2009 | King |
| 2009/0043240 A1 | 2/2009 | Robinson et al. |
| 2009/0054753 A1 | 2/2009 | Robinson et al. |
| 2009/0069743 A1 | 3/2009 | Krishnamoorthy et al. |
| 2009/0069745 A1 | 3/2009 | Estes et al. |
| 2009/0069787 A1 | 3/2009 | Estes et al. |
| 2009/0099521 A1 | 4/2009 | Gravesen et al. |
| 2009/0105573 A1 | 4/2009 | Malecha |
| 2009/0131861 A1 | 5/2009 | Braig et al. |
| 2009/0156922 A1 | 6/2009 | Goldberger et al. |
| 2009/0156924 A1 | 6/2009 | Shariati et al. |
| 2009/0163781 A1 | 6/2009 | Say et al. |
| 2009/0198350 A1 | 8/2009 | Thiele |
| 2009/0221890 A1 | 9/2009 | Saffer et al. |
| 2009/0228214 A1 | 9/2009 | Say et al. |
| 2009/0318791 A1 | 12/2009 | Kaastrup |

(56) References Cited

U.S. PATENT DOCUMENTS

| | | |
|---|---|---|
| 2009/0326343 A1 | 12/2009 | Gable et al. |
| 2010/0057042 A1 | 3/2010 | Hayter |
| 2010/0114026 A1 | 5/2010 | Karratt et al. |
| 2010/0121170 A1 | 5/2010 | Rule |
| 2010/0137784 A1 | 6/2010 | Cefai et al. |
| 2010/0152658 A1 | 6/2010 | Hanson et al. |
| 2010/0174228 A1 | 7/2010 | Buckingham et al. |
| 2010/0211003 A1 | 8/2010 | Sundar et al. |
| 2010/0228110 A1 | 9/2010 | Tsoukalis |
| 2010/0262117 A1 | 10/2010 | Magni et al. |
| 2010/0262434 A1 | 10/2010 | Shaya |
| 2010/0295686 A1 | 11/2010 | Sloan et al. |
| 2010/0298765 A1 | 11/2010 | Budiman et al. |
| 2011/0021584 A1 | 1/2011 | Berggren et al. |
| 2011/0028817 A1 | 2/2011 | Jin et al. |
| 2011/0054390 A1 | 3/2011 | Searle et al. |
| 2011/0054399 A1 | 3/2011 | Chong et al. |
| 2011/0124996 A1 | 5/2011 | Reinke et al. |
| 2011/0144586 A1 | 6/2011 | Michaud et al. |
| 2011/0160652 A1 | 6/2011 | Yodfat et al. |
| 2011/0178472 A1 | 7/2011 | Cabiri |
| 2011/0190694 A1 | 8/2011 | Lanier, Jr. et al. |
| 2011/0202005 A1 | 8/2011 | Yodfat et al. |
| 2011/0218495 A1 | 9/2011 | Remde |
| 2011/0230833 A1 | 9/2011 | Landman et al. |
| 2011/0251509 A1 | 10/2011 | Beyhan et al. |
| 2011/0313680 A1 | 12/2011 | Doyle et al. |
| 2011/0316562 A1 | 12/2011 | Cefai et al. |
| 2012/0003935 A1 | 1/2012 | Lydon et al. |
| 2012/0010594 A1 | 1/2012 | Holt et al. |
| 2012/0030393 A1 | 2/2012 | Ganesh et al. |
| 2012/0053556 A1 | 3/2012 | Lee |
| 2012/0078067 A1 | 3/2012 | Kovatchev et al. |
| 2012/0078161 A1 | 3/2012 | Masterson et al. |
| 2012/0078181 A1 | 3/2012 | Smith et al. |
| 2012/0101451 A1 | 4/2012 | Boit et al. |
| 2012/0123234 A1 | 5/2012 | Atlas et al. |
| 2012/0136336 A1 | 5/2012 | Mastrototaro et al. |
| 2012/0190955 A1 | 7/2012 | Rao et al. |
| 2012/0203085 A1 | 8/2012 | Rebec |
| 2012/0203178 A1 | 8/2012 | Tverskoy |
| 2012/0215087 A1 | 8/2012 | Cobelli et al. |
| 2012/0225134 A1 | 9/2012 | Komorowski |
| 2012/0226259 A1 | 9/2012 | Yodfat et al. |
| 2012/0232520 A1 | 9/2012 | Sloan et al. |
| 2012/0238851 A1 | 9/2012 | Kamen et al. |
| 2012/0271655 A1 | 10/2012 | Knobel et al. |
| 2012/0277668 A1 | 11/2012 | Chawla |
| 2012/0282111 A1 | 11/2012 | Nip et al. |
| 2012/0295550 A1 | 11/2012 | Wilson et al. |
| 2013/0030358 A1 | 1/2013 | Yodfat et al. |
| 2013/0085772 A1* | 4/2013 | Gaweda ................ G16Z 99/00 705/2 |
| 2013/0158503 A1 | 6/2013 | Kanderian, Jr. et al. |
| 2013/0178791 A1 | 7/2013 | Javitt |
| 2013/0231642 A1 | 9/2013 | Doyle et al. |
| 2013/0253472 A1 | 9/2013 | Cabiri |
| 2013/0261406 A1 | 10/2013 | Rebec et al. |
| 2013/0296823 A1 | 11/2013 | Melker et al. |
| 2013/0317753 A1 | 11/2013 | Kamen et al. |
| 2013/0338576 A1 | 12/2013 | OConnor et al. |
| 2014/0005633 A1 | 1/2014 | Finan |
| 2014/0066886 A1 | 3/2014 | Roy et al. |
| 2014/0074033 A1 | 3/2014 | Sonderegger et al. |
| 2014/0121635 A1 | 5/2014 | Hayter |
| 2014/0128839 A1 | 5/2014 | Dilanni et al. |
| 2014/0135880 A1 | 5/2014 | Baumgartner et al. |
| 2014/0146202 A1 | 5/2014 | Boss et al. |
| 2014/0180203 A1 | 6/2014 | Budiman et al. |
| 2014/0180240 A1 | 6/2014 | Finan et al. |
| 2014/0200426 A1 | 7/2014 | Taub et al. |
| 2014/0200559 A1 | 7/2014 | Doyle et al. |
| 2014/0230021 A1 | 8/2014 | Birtwhistle et al. |
| 2014/0276554 A1 | 9/2014 | Finan et al. |
| 2014/0276556 A1 | 9/2014 | Saint et al. |
| 2014/0278123 A1 | 9/2014 | Prodhom et al. |
| 2014/0309615 A1 | 10/2014 | Mazlish |
| 2014/0316379 A1 | 10/2014 | Sonderegger et al. |
| 2014/0325065 A1 | 10/2014 | Birtwhistle et al. |
| 2015/0018633 A1 | 1/2015 | Kovachev et al. |
| 2015/0025329 A1 | 1/2015 | Amarasingham et al. |
| 2015/0025495 A1 | 1/2015 | Peyser |
| 2015/0120317 A1 | 4/2015 | Mayou et al. |
| 2015/0134265 A1 | 5/2015 | Kohlbrecher et al. |
| 2015/0165119 A1 | 6/2015 | Palerm et al. |
| 2015/0173674 A1 | 6/2015 | Hayes et al. |
| 2015/0213217 A1 | 7/2015 | Amarasingham et al. |
| 2015/0217052 A1 | 8/2015 | Keenan et al. |
| 2015/0217053 A1 | 8/2015 | Booth et al. |
| 2015/0265767 A1 | 9/2015 | Vazquez et al. |
| 2015/0306314 A1 | 10/2015 | Doyle et al. |
| 2015/0351671 A1 | 12/2015 | Vanslyke et al. |
| 2015/0366945 A1 | 12/2015 | Greene |
| 2016/0015891 A1 | 1/2016 | Papiorek |
| 2016/0038673 A1 | 2/2016 | Morales |
| 2016/0038689 A1 | 2/2016 | Lee et al. |
| 2016/0051749 A1 | 2/2016 | Istoc |
| 2016/0082187 A1 | 3/2016 | Schaible et al. |
| 2016/0089494 A1 | 3/2016 | Guerrini |
| 2016/0175520 A1* | 6/2016 | Palerm ................ A61M 5/1723 604/504 |
| 2016/0228641 A1 | 8/2016 | Gescheit et al. |
| 2016/0243318 A1 | 8/2016 | Despa et al. |
| 2016/0256087 A1 | 9/2016 | Doyle et al. |
| 2016/0287512 A1 | 10/2016 | Cooper et al. |
| 2016/0302054 A1 | 10/2016 | Kimura et al. |
| 2016/0331310 A1 | 11/2016 | Kovatchev |
| 2016/0354543 A1 | 12/2016 | Cinar et al. |
| 2017/0049386 A1 | 2/2017 | Abraham et al. |
| 2017/0143899 A1 | 5/2017 | Gondhalekar et al. |
| 2017/0143900 A1 | 5/2017 | Rioux et al. |
| 2017/0156682 A1 | 6/2017 | Doyle et al. |
| 2017/0173261 A1 | 6/2017 | OConnor et al. |
| 2017/0189625 A1 | 7/2017 | Cirillo et al. |
| 2017/0281877 A1 | 10/2017 | Marlin et al. |
| 2017/0296746 A1 | 10/2017 | Chen et al. |
| 2017/0311903 A1 | 11/2017 | Davis et al. |
| 2017/0348482 A1* | 12/2017 | Duke ................ A61B 5/14532 |
| 2018/0036495 A1 | 2/2018 | Searle et al. |
| 2018/0040255 A1 | 2/2018 | Freeman et al. |
| 2018/0075200 A1 | 3/2018 | Davis et al. |
| 2018/0075201 A1 | 3/2018 | Davis et al. |
| 2018/0075202 A1 | 3/2018 | Davis et al. |
| 2018/0092576 A1 | 4/2018 | Ambrosio |
| 2018/0126073 A1 | 5/2018 | Wu et al. |
| 2018/0169334 A1 | 6/2018 | Grosman et al. |
| 2018/0200434 A1 | 7/2018 | Mazlish et al. |
| 2018/0200438 A1 | 7/2018 | Mazlish et al. |
| 2018/0200441 A1 | 7/2018 | Desborough et al. |
| 2018/0204636 A1 | 7/2018 | Edwards et al. |
| 2018/0277253 A1 | 9/2018 | Gondhalekar et al. |
| 2018/0289891 A1 | 10/2018 | Finan et al. |
| 2018/0296757 A1 | 10/2018 | Finan et al. |
| 2018/0342317 A1 | 11/2018 | Skirble et al. |
| 2018/0369479 A1 | 12/2018 | Hayter et al. |
| 2019/0076600 A1 | 3/2019 | Grosman et al. |
| 2019/0240403 A1 | 8/2019 | Palerm et al. |
| 2019/0290844 A1 | 9/2019 | Monirabbasi et al. |
| 2019/0336683 A1 | 11/2019 | O'Connor et al. |
| 2019/0336684 A1 | 11/2019 | OConnor et al. |
| 2019/0348157 A1 | 11/2019 | Booth et al. |
| 2020/0046268 A1 | 2/2020 | Patek et al. |
| 2020/0101222 A1 | 4/2020 | Lintereur et al. |
| 2020/0101223 A1 | 4/2020 | Lintereur et al. |
| 2020/0101225 A1 | 4/2020 | OConnor et al. |
| 2020/0219625 A1 | 7/2020 | Kahlbaugh |
| 2020/0342974 A1 | 10/2020 | Chen et al. |
| 2021/0050085 A1 | 2/2021 | Hayter et al. |

(56) References Cited

U.S. PATENT DOCUMENTS

| | | |
|---|---|---|
| 2021/0098105 A1 | 4/2021 | Lee et al. |
| 2022/0023536 A1 | 1/2022 | Graham et al. |

FOREIGN PATENT DOCUMENTS

| | | |
|---|---|---|
| CN | 1297140 A | 5/2001 |
| DE | 19756872 A1 | 7/1999 |
| EP | 0341049 A2 | 11/1989 |
| EP | 0496305 A2 | 7/1992 |
| EP | 0549341 A1 | 6/1993 |
| EP | 1491144 A1 | 12/2004 |
| EP | 1571582 A2 | 9/2005 |
| EP | 0801578 B1 | 7/2006 |
| EP | 2139382 A1 | 1/2010 |
| EP | 2397181 A1 | 12/2011 |
| EP | 2666520 A1 | 11/2013 |
| EP | 2695573 A2 | 2/2014 |
| EP | 2830499 A1 | 2/2015 |
| EP | 2943149 A1 | 11/2015 |
| EP | 3177344 A1 | 6/2017 |
| EP | 3314548 A1 | 5/2018 |
| EP | 2897071 B1 | 5/2019 |
| EP | 3607985 A1 | 2/2020 |
| GB | 2443261 A | 4/2008 |
| JP | 51125993 A | 11/1976 |
| JP | 02131777 A | 5/1990 |
| JP | 2004283378 A | 10/2007 |
| JP | 2017525451 A | 9/2017 |
| JP | 2018153569 A | 10/2018 |
| JP | 2019525276 A | 9/2019 |
| TW | 200740148 A | 10/2007 |
| TW | M452390 U | 5/2013 |
| WO | 9800193 A1 | 1/1998 |
| WO | 9956803 A1 | 11/1999 |
| WO | 0030705 A1 | 6/2000 |
| WO | 0032258 A1 | 6/2000 |
| WO | 0172354 A2 | 10/2001 |
| WO | 2002015954 A1 | 2/2002 |
| WO | 0243866 A2 | 6/2002 |
| WO | 02082990 A1 | 10/2002 |
| WO | 03016882 A1 | 2/2003 |
| WO | 03039362 A1 | 5/2003 |
| WO | 03045233 A1 | 6/2003 |
| WO | 2004043250 A1 | 5/2004 |
| WO | 2004092715 A1 | 10/2004 |
| WO | 2005051170 A2 | 6/2005 |
| WO | 2005082436 A1 | 9/2005 |
| WO | 05110601 A1 | 11/2005 |
| WO | 2005113036 A1 | 12/2005 |
| WO | 2006053007 A2 | 5/2006 |
| WO | 2007064835 A2 | 6/2007 |
| WO | 2007078937 A1 | 7/2007 |
| WO | 2008024810 A2 | 2/2008 |
| WO | 2008029403 A1 | 3/2008 |
| WO | 2008133702 A1 | 11/2008 |
| WO | 2009045462 A1 | 4/2009 |
| WO | 2009049252 A1 | 4/2009 |
| WO | 2009066287 A3 | 5/2009 |
| WO | 2009066288 A1 | 5/2009 |
| WO | 2009098648 A2 | 8/2009 |
| WO | 2009134380 A2 | 11/2009 |
| WO | 2010053702 A1 | 5/2010 |
| WO | 2010132077 A1 | 11/2010 |
| WO | 2010138848 A1 | 12/2010 |
| WO | 2010147659 A2 | 12/2010 |
| WO | 2011095483 A1 | 8/2011 |
| WO | 2012045667 A2 | 4/2012 |
| WO | 2012108959 A1 | 8/2012 |
| WO | 2012134588 A1 | 10/2012 |
| WO | 2012177353 A1 | 12/2012 |
| WO | 2012178134 A2 | 12/2012 |
| WO | 2013078200 A1 | 5/2013 |
| WO | 2013134486 A2 | 9/2013 |
| WO | 20130149186 A1 | 10/2013 |
| WO | 2013177565 A1 | 11/2013 |
| WO | 2013182321 A1 | 12/2013 |
| WO | 2014109898 A1 | 7/2014 |
| WO | 2014110538 A1 | 7/2014 |
| WO | 2014194183 A2 | 12/2014 |
| WO | 2015056259 A1 | 4/2015 |
| WO | 2015061493 A1 | 4/2015 |
| WO | 2015073211 A1 | 5/2015 |
| WO | 2015081337 A2 | 6/2015 |
| WO | 2015187366 A1 | 12/2015 |
| WO | 2016004088 A1 | 1/2016 |
| WO | 2016022650 A1 | 2/2016 |
| WO | 2016041873 A1 | 3/2016 |
| WO | 2016089702 A1 | 6/2016 |
| WO | 2016141082 A1 | 9/2016 |
| WO | 2016161254 A1 | 10/2016 |
| WO | 2017004278 A1 | 1/2017 |
| WO | 2017091624 A1 | 6/2017 |
| WO | 2017105600 A1 | 6/2017 |
| WO | 2017184988 A1 | 10/2017 |
| WO | 2017205816 A1 | 11/2017 |
| WO | 2018009614 A1 | 1/2018 |
| WO | 2018067748 A1 | 4/2018 |
| WO | 2018120104 A1 | 7/2018 |
| WO | 2018136799 A1 | 7/2018 |
| WO | 2018204568 A1 | 11/2018 |
| WO | 2019/016452 A1 | 1/2019 |
| WO | 2019077482 A1 | 4/2019 |
| WO | 2019094440 A1 | 5/2019 |
| WO | 2019213493 A1 | 11/2019 |
| WO | 2019246381 A1 | 12/2019 |
| WO | 2020081393 A1 | 4/2020 |
| WO | 2021011738 A1 | 1/2021 |

OTHER PUBLICATIONS

Unger, Jeff, et al., "Glucose Control in the Hospitalized Patient," Emerg. Med 36(9):12-18 (2004).
Glucommander FAQ downloaded from https://adaendo.com/GlucommanderFAQ.html on Mar. 16, 2009.
Finfer, Simon & Heritier, Stephane. (2009). The NICE-SUGAR (Normoglycaemia in Intensive Care Evaluation and Survival Using Glucose Algorithm Regulation) Study: statistical analysis plan. Critical care and resuscitation : journal of the Australasian Academy of Critical Care Medicine. 11. 46-57.
Letters to the Editor regarding "Glucose Control in Critically Ill Patients," N Engl J Med 361: 1, Jul. 2, 2009.
"Medtronic is Leading a Highly Attractive Growth Market," Jun. 2, 2009.
Davidson, Paul C., et al. "Glucommander: An Adaptive, Computer-Directed System for IV Insulin Shown to be Safe, Simple, and Effective in 120,618 Hours of Operation," Atlanta Diabetes Associates presentation Nov. 16, 2003.
Davidson, Paul C., et al. "Pumpmaster and Glucommander," presented at the MiniMed Symposium, Atlanta GA, Dec. 13, 2003.
Kanji S., et al. "Reliability of point-of-care testing for glucose measurement in critically ill adults," Critical Care Med, vol. 33, No. 12, pp. 2778-2785, 2005.
Krinsley James S., "Severe hypoglycemia in critically ill patients: Risk factors and outcomes," Critical Care Med, vol. 35, No. 10, pp. 1-6, 2007.
International Searching Authority, Invitation to Pay Additional Fees, International Application No. PCT/US2006/004929, dated Jul. 27, 2006.
Farkas et al. ""Single-Versus Triple-Lumen Central Catheter-Related Sepsis: A Prospective Randomized Study in a Critically Ill Population"" The American Journal of Medicine Sep. 1992vol. 93 p. 277-282.
Davidson, Paul C., et al., A computer-directed intravenous insulin system shown to be safe, simple,and effective in 120,618 h of operation. Diabetes Care, vol. 28, No. 10, Oct. 2005, pp. 2418-2423.
International Search Report and Written Opinion for the International Patent Application No. PCT/US2021/016283, dated Jun. 2, 2021, 15 pages.

(56) References Cited

OTHER PUBLICATIONS

Gorke, A. "Microbial contamination of haemodialysis catheter connections." EDTNA/ERCA journal (English ed.) vol. 31,2 (2005): 79-84. doi:10.1111/j.1755-6686.2005.tb00399.x.

Lovich et al. "Central venous catheter infusions: A laboratory model shows large differences in drug delivery dynamics related to catheter dead volume" Critical Care Med 2007 vol. 35, No. 12.

Van Den Berghe, Greet, M.D., Ph.D., et al., Intensive Insulin Therapy in Critically Ill Patients, The New England Journal of Medicine, vol. 345, No. 19, Nov. 8, 2001, pp. 1359-1367.

Templeton et al, "Multilumen Central Venous Catheters Increase Risk for Catheter-Related Bloodstream Infection: Prospective Surveillance Study" Infection 2008; 36: 322-327.

Wilson, George S., et al., Progress toward the Development of an Implantable Sensor for Glucose, Clin. Chem., vol. 38, No. 9, 1992, pp. 1613-1617.

Yeung et al. "Infection Rate for Single Lumen v Triple Lumen Subclavian Catheters" Infection Control and Hospital Epidemiology, vol. 9, No. 4 (Apr. 1988) pp. 154-158 The University of Chicago Press.

International Search Report and Written Opinion, International Application No. PCT/US2010/033794 dated Jul. 16, 2010.

International Search Report and Written Opinion in PCT/US2008/079641 dated Feb. 25, 2009.

Berger, ""Measurement of Analytes in Human Serum and Whole Blood Samples by Near-Infrared Raman Spectroscopy,"" Ph D. Thesis, Massachusetts Institute of Technology, Chapter 4, pp. 50-73,1998.

Berger, "An Enhanced Algorithm for Linear Multivariate Calibration," Analytical Chemistry, vol. 70, No. 3, pp. 623-627, Feb. 1, 1998.

Billman et al.,"Clinical Performance of an In line Ex-Vivo Point of Care Monitor: A Multicenter Study," Clinical Chemistry 48: 11, pp. 2030-2043, 2002.

Widness et al., "Clinical Performance on an In-Line Point-of-Care Monitor in Neonates"; Pediatrics, vol. 106, No. 3, pp. 497-504, Sep. 2000.

Finkielman et al., "Agreement Between Bedside Blood and Plasma Glucose Measurement in the ICU Setting" retrieved from http://www.chestjournal.org; CHEST/127/5/May 2005.

Glucon Critical Care Blood Glucose Monitor; Glucon; retrieved from http://www.glucon.com.

Fogt, et al., "Development and Evaluation of a Glucose Analyzer for a Glucose-Controlled Insulin Infusion System (Biostator)"; Clinical Chemistry, vol. 24, No. 8, pp. 1366-1372, 1978.

Vonach et al., "Application of Mid-Infrared Transmission Spectrometry to the Direct Determination of Glucose in Whole Blood," Applied Spectroscopy, vol. 52, No. 6, 1998, pp. 820-822.

Muniyappa et al., "Current Approaches for assessing insulin sensitivity and resistance in vivo: advantages, limitations, and appropriate usage," AJP—Endocrinol Metab, vol. 294, E15-E26, first published Oct. 23, 2007.

R Anthony Shaw, et al., "Infrared Spectroscopy in Clinical and Dianostic Analysis," Encyclopedia of Analytical Chemistry, ed. Robert A. Meyers, John Wiley & Sons, Ltd., pp. 1-20, 2000.

International Preliminary Report on Patentability for the International Patent Application No. PCT/US2019/053603, dated Apr. 8, 2021, 9 pages.

International Search Report and Written Opinion for the International Patent Application No. PCT/US2019/053603, dated Jan. 7, 2020, 16 pages.

Dassau et al., "Detection of a meal using continuous glucose monitoring: Implications for an artificial [beta]-cell." Diabetes Care, American Diabetes Association, Alexandria, VA, US, 31(2):295-300 (2008).

Cameron et al., "Probabilistic Evolving Meal Detection and Estimation of Meal Total Glucose Appearance Author Affiliations", J Diabetes Sci and Tech,vol. Diabetes Technology Society ;(5):1022-1030 (2009).

Lee et al., "A closed-loop artificial pancreas based on model predictive control: Human-friendly identification and automatic meal disturbance rejection", Biomedical Signal Processing and Control, Elsevier, Amsterdam, NL, 4(4):1746-8094 (2009).

International Search Report and Written Opinion for the InternationalPatent Application No. PCT/US2021/018297, dated May 18, 2021, 18 pages.

An Emilia Fushimi: "Artificial Pancreas: Evaluating the ARG Algorithm Without Meal Announcement", Journal of Diabetes Science and Technology Diabetes Technology Society, Mar. 22, 2019, pp. 1025-1043.

International Search Report and Written Opinion for the International Patent Application No. PCT/US2021/017441, dated May 25, 2021, 12 pages.

International Search Report and Written Opinion for the InternationalPatent Application No. PCT/US2021/017664, dated May 26, 2021, 16 pages.

Mirko Messori et al: "Individualized model predictive control for the artificial pancreas: In silico evaluation of closed-loop glucose control", IEEE Control Systems, vol. 38, No. 1, Feb. 1, 2018, pp. 86-104.

International Search Report and Written Opinion for the International Patent Application No. PCT/US2021/017662, dated May 26, 2021, 14 pages.

Anonymous: "Reservoir Best Practice and Top Tips" Feb. 7, 2016, URL: https://www.medtronic-diabetes.co.uk/blog/reservoir-best-practice-and-top-tips, p. 1.

Gildon Bradford: "InPen Smart Insulin Pen System: Product Review and User Experience" Diabetes Spectrum, vol. 31, No. 4, Nov. 15, 2018, pp. 354-358.

International Search Report and Written Opinion for the International Patent Application No. PCT/US2021/016050, dated May 27, 2021, 16 pages.

International Search Report and Written Opinion for the International Patent Application No. PCT/US2020/065226, dated May 31, 2021, 18 pages.

International Search Report and Written Opinion for the International Patent Application No. PCT/US2021/017659, dated May 31, 2021, 13 pages.

Miontaser Eslam et al., "Seasonal Local Models for Glucose Prediction in Type 1 Diabetes", IEE Journal of Biomedical and Health Informatics, IEEE, Piscataway, NJ, USA, vol. 24, No. 7, Jul. 2020, pp. 2064-2072.

Samadi Sediqeh et al., "Automatic Detection and Estimation of Unannouced Meals for Multivariable Artificial Pancreas System", Diabetis Technology & Therapeutics, vol. 20m No. 3, Mar. 1, 2018, pp. 235-246.

Samadi Sediqeh et al., "Meal Detection and Carbohydrate Estimation Using Continuous Glucose Sensor Data" IEEE Journal of Biomedical and Health Informatics, IEEE, Piscataway, NJ, USA, vol. 21, No. 3, May 1, 2017, pp. 619-627.

Khodaei et al., "Physiological Closed-Loop Contol (PCLC) Systems: Review of a Modern Frontier in Automation", IEEE Access, IEEE, USA, vol. 8, Jan. 20, 2020, pp. 23965-24005.

E. Atlas et al., "MD-Logic Artificial Pancreas System: A pilot study in adults with type 1 diabetes", Diabetes Care, vol. 33, No. 5, Feb. 11, 2010, pp. 1071-1076.

Anonymous: "Fuzzy control system", Wikipedia, Jan. 10, 2020. URL: https://en.wikipedia.org/w/index.php?title=Fuzzy_control_system&oldid=935091190 Retrieved: May 25, 2021.

International Search Report and Written Opinion for the International Patent Application No. PCT/US2021/022694, dated Jun. 25, 2021, 13 pages.

International Search Report and Written Opinion for the International Patent Application No. PCT/US2020/052125, dated Aug. 12, 2020, 15 pages.

International Search Report and Written Opinion for the International Patent Application No. PCT/US2020/050332, dated Sep. 12, 2020, 12 pages.

European Patent Office, "Notification of Transmittal of the ISR and the Written Opinion of the International Searching Authority, or the Declaration," in PCT Application No. PCT/GB2015/050248, dated Jun. 23, 2015, 12 pages.

(56) References Cited

OTHER PUBLICATIONS

Anonymous: "Artificial pancreas—Wikipedia", Mar. 13, 2018 (Mar. 13, 2018), XP055603712, Retrieved from the Internet: URL: https://en.wikipedia.org/wiki/Artificial_pancreas [retrieved on Jul. 9, 2019] section "Medical Equipment" and the figure labeled "The medical equipment approach to an artifical pancreas".

Kaveh et al., "Blood Glucose Regulation via Double Loop Higher Order Sliding Mode Control and Multiple Sampling Rate." Paper presented at the proceedings of the 17th IFAC World Congress, Seoul, Korea (Jul. 2008).

Dassau et al., "Real-Time Hypoglycemia Prediction Suite Using Contineous Glucose Monitoring," Diabetes Care, vol. 33, No. 6, 1249-1254 (2010).

International Search Report and Written Opinion for International Patent Application No. PCT/US17/53262, dated Dec. 13, 2017, 8 pages.

Van Heusden et al., "Control-Relevant Models for Glucose Control using A Priori Patient Characteristics", IEEE Transactions on Biomedical Engineering, vol. 59, No. 7, (Jul. 1, 2012) pp. 1839-1849.

Doyle III et al., "Run-to-Run Control Strategy for Diabetes Management." Paper presented at 23rd Annual International Conference of the IEEE Engineering in Medicine and Biology Society, Istanbul, Turkey (Oct. 2001).

Bequette, B.W., and Desemone, J., "Intelligent Dosing Systems": Need for Design and Analysis Based on Control Theory, Diabetes Technology and Therapeutics 9(6): 868-873 (2004).

Parker et al., "A Model-Based Agorithm for Blood Gucose Control in Type 1 Diabetic Patients." IEEE Transactions on Biomedical Engineering, 46 (2) 148-147 (1999).

International Search Report and Written Opinion for International Patent Application No. PCT/US2017/015601, dated May 16, 2017, 12 pages.

International Search Report and Written Opinion for the International Patent Application No. PCT/US2018/018901, dated Aug. 6, 2018, 12 pages.

International Search Report and Written Opinion for International Patent Application No. PCT/US2018/052467, dated Jan. 4, 2019, 13 pages.

"How to Create a QR Code that Deep Links to Your Mobile App", Pure Oxygen Labs, web<https://pureoxygenlabs.com/how-to-create-a-qr-codes-that-deep-link-to-your-mobile-app/> Year:2017.

"Read NFC Tags with an iPHone App on iOS 11", GoToTags, Sep. 11, 2017, web <https://gototags.com/blog/read-nfc-tags-with-an-iphone-app-on-ios-11/>. (Year:2017).

International Search Report and Written Opinion for International Patent Application No. PCT/US2016/063350, dated Mar. 27, 2017, 9 pages.

Extended Search Report dated Aug. 13, 2018, issued in European Patent Application No. 16753053.4, 9 pages.

International Search Report and Written Opinion for International Patent Application No. PCT/US16/18452, dated Apr. 29, 2015, 9 pages.

International Preliminary Report on Patentability dated Aug. 31, 2017, issued in PCT Patent Application No. PCT/US2016/018452, 7 pages.

International Search Report and Written Opinion for International Patent Application No. PCT/US2019/055862, dated Mar. 11, 2020.

European Search Report for the European Patent Application No. 21168591.2, dated Oct. 13, 2021, 4 pages.

International Search Report and Written Opinion for the International Patent Application No. PCT/US2021/041954, dated Oct. 25, 2021, 13 pages.

International Search Report and Written Opinion for the International Patent Application No. PCT/US2021/047771, dated Dec. 22, 2021, 11 pages.

International Search Report and Written Opinion for the International Patent Application No. PCT/US2021/052855, dated Dec. 22, 2021, 11 pages.

International Search Report and Written Opinion for International Patent Application No. PCT/US2021/051027, dated Jan. 7, 2022, 16 pages.

International Search Report and Written Opinion for International Patent Application No. PCT/US2021/052372, dated Jan. 26, 2022, 15 pages.

International Search Report and Written Opinion for the International Patent Application No. PCT/US2021/046607, dated Jan. 31, 2022, 20 pages.

International Search Report and Written Opinion for the International Patent Application No. PCT/US2021/055745, dated Feb. 14, 2022, 13 pages.

International Search Report and Written Opinion for the International Patent Application No. PCT/US2022/013470, dated May 6, 2022, 14 pages.

International Search Report and Written Opinion for the International Patent Application No. PCT/US2022/013473, dated May 6, 2022, 13 pages.

International Search Report and Written Opinion for the International Patent Application No. PCT/US2022/019079, dated Jun. 2, 2022, 14 pages.

International Search Report and Written Opinion for the International Patent Application No. PCT/US2022/018453, dated Jun. 2, 2022, 13 pages.

International Search Report and Written Opinion for the International Patent Application No. PCT/US22/018700, dated Jun. 7, 2022, 13 pages.

International Search Report and Written Opinion for the International Patent Application No. PCT/US22/019080, dated Jun. 7, 2022, 14 pages.

International Search Report and Written Opinion for the International Patent Application No. PCT/US22/019664, dated Jun. 7, 2022, 14 pages.

International Search Report and Written Opinion for the International Patent Application No. PCT/US21/060618, dated Mar. 21, 2022, 15 pages.

Herrero Pau et al: "Enhancing automatic closed-loop glucose control in type 1 diabetes with an adaptive meal polus calculator—in silicoevaluation under intra-day variability", Computer Methods and Programs in Biomedicine, Elsevier, Amsterdam, NL, vol. 146, Jun. 1, 2017 (Jun. 1, 2017), pp. 125-131, XP085115607, ISSN: 0169-2607, DOI:10.1016/J.CMPB.2017.05.010.

Marie Aude Qemerais: "Preliminary Evaluation of a New Semi-Closed-Loop Insulin Therapy System over the prandial beriod in Adult Patients with type I diabetes: the WP6. 0 Diabeloop Study", Journal of Diabetes Science and Technology Diabetes Technology Society Reprints and permissions, Jan. 1, 2014, pp. 1177-1184, Retrieved from the Internet: URL:http://journals.sagepub.com/doi/pdf/10.1177/1932296814545668 [retrieved on Jun. 6, 2022] chapter "Functioning of the Algorithm" chapter "Statistical Analysis" p. 1183, left-hand column, line 16-line 23.

Anonymous: "Kernel density estimation", Wikipedia, Nov. 13, 2020 (Nov. 13, 2020), pp. 1-12, XP055895569, Retrieved from the Internet: URL:https://en.wikipedia.org/w/index.php?title=Kernel_density_estimation&oldid=988508333 [retrieved on Jun. 6, 2022].

Anonymous: "openaps / oref0 /lib/determine-basal-js", openaps repository, Nov. 9, 2019 (Nov. 9, 2019), pp. 1-17, XP055900283, Retrieved from the Internet: URL:https://github.com/openaps/oref0/blob/master/lib/determine-basal/determine-basal.js [retrieved on Jun. 6, 2022] line 116-line 118, line 439-line 446.

Anonymous: "AndroidAPS screens", AndroidAPS documentation, Oct. 4, 2020 (Oct. 4, 2020), pp. 1-12, XP055894824, Retrieved from the Internet: URL:https://github.com/openaps/AndroidAPSdocs/blob/25d8acf8b28262b411b34f416f173ac0814d7e14/docs/EN/Getting-Started/Screenshots.md [retrieved on Jun.6, 2022].

Kozak Milos et al.: "Issue #2473 of AndroidAPS", MilosKozak / AndroidAPS Public repository, Mar. 4, 2020 (Mar. 4, 2020), pp. 1-4, XP055900328, Retrieved from the Internet: URL:https://github.com/MilosKozak/AndroidAPS/issues/2473 [retrieved on Jun. 6, 2022].

Medication Bar Code System Implementation Planning Section I: A Bar Code Primer for Leaders, Aug. 2013.

(56) References Cited

OTHER PUBLICATIONS

Medication Bar Code System Implementation Planning Section II: Building the Case for Automated Identification of Medications, Aug. 2013.

Villareal et al. (2009) in: Distr. Comp. Art. Intell. Bioninf. Soft Comp. Amb. Ass. Living; Int. Work Conf. Art. Neural Networks (IWANN) 2009, Lect. Notes Comp. Sci. vol. 5518; S. Omatu et al. (Eds ), pp. 870-877.

Fox, Ian G.; Machine Learning for Physiological Time Series: Representing and Controlling Blood Glucose for Diabetes Management; University of Michigan. ProQuest Dissertations Publishing, 2020. 28240142. (Year: 2020).

International Search Report and Written Opinion for the International Patent Application No. PCT/US2022/012896, dated Apr. 22, 2022, 15 pages.

* cited by examiner

400

Receive a number of blood glucose measurement values over a period of time

415

Determine a correction bolus dosage of insulin is required by a user based on an evaluation of the number of blood glucose measurement values

425

Obtain a final insulin value of the correction bolus dosage based on an output of a function

435

Set an insulin bolus dosage based on the obtained final insulin value

445

455

Actuate delivery of insulin according to the set insulin bolus dosage

```
Calculate a difference between the selected blood glucose measurement value and the
target blood glucose value of the user
```
↘ 510

```
Determine which of the calculated difference or a maximum correction blood glucose value
is a lower blood glucose value
```
↘ 520

```
Apply an insulin adjustment factor to the lower blood glucose value
```
↘ 530

```
Output a result of the applying the insulin adjustment factor to the lower blood glucose
value
```
↘ 540

FIG. 5

BLOOD GLUCOSE RATE OF CHANGE MODULATION OF MEAL AND CORRECTION INSULIN BOLUS QUANTITY

TECHNICAL FIELD

The described examples provide features for a drug delivery system that accounts for a rate of change in blood glucose measurement values.

BACKGROUND

Drug or therapeutic agent delivery systems typically deliver a drug or therapeutic agent to a user based on health conditions of the user. However, because of the complicated and dynamic nature of the human body's response to insulin, it is not uncommon for patients to end up in a hypoglycemic or hyperglycemic state after providing themselves with a meal or correction bolus. This outcome is undesirable for many reasons: hypoglycemia creates an immediate risk of a severe medical event (seizure, coma, death) while hyperglycemia creates long term negative health effects as well as the risk of ketoacidosis. Whether a patient ends up hypoglycemic, hyperglycemic, or within range after a bolus depends on many things including how fast, and in which direction, your blood glucose is changing. If a patient uses a typical finger stick test to assess blood glucose, they typically do not have the blood glucose rate of change information due to the infrequent nature of the tests. If a patient is wearing a continuous glucose monitor (CGM) they will typically have enough data to have an accurate blood glucose rate of change value. Yet, due to the lag time between 1) the bodies interstitial fluid response to blood glucose changes, 2) the CGM providing a blood glucose value, and 3) a patient using the data to determine an insulin treatment quantity there may be a significant difference between the CGM blood glucose value the patient is using to calculate their insulin treatment and the patient's actual blood glucose. This difference may cause the patient to become hypoglycemic or hyperglycemic after their insulin treatment, depending on the magnitude and direction of the blood glucose rate of change. Of the two scenarios, hypoglycemia is seen to be the less desirable and more dangerous of the two.

Systems are available that apply a percentage increase/decrease to the final insulin amount based on rate of change. These systems assign a bonus (or reduction) percentage, such as plus or minus 30 percent, of insulin based on the patient's blood glucose rate of change. While this has proven to be effective, the blanket adjustment is still not optimal and is not as effective for correction boluses, particularly, correction boluses taken to compensate for consumption of a meal. Therefore, there is a need to provide more effective correction bolus dosages that may result in a reduced amount of time a patient may be in a hypoglycemic state.

SUMMARY

Disclosed is an example of a non-transitory computer readable medium that is embodied with programming code executable by a processor. The processor when executing the programming code is operable to perform functions that include receiving a number of blood glucose measurement values over a period of time. A correction bolus dosage based on a latest blood glucose measurement value of the number of blood glucose measurement values may be calculated. A rate of change of blood glucose values may be determined from the number of blood glucose measurement values over the period of time. A revised bolus dosage using the determined rate of change and the latest blood glucose measurement value may be calculated. A function may be applied to the correction bolus dosage and the revised bolus dosage, and, based on an output from the function, a final insulin value may be determined. An insulin bolus dosage may be set using the determined final insulin value, and delivery of insulin according to the set insulin bolus dosage may be actuated.

Disclosed is a device including a processor, a memory, and a transceiver. The processor when executing the artificial pancreas application is operable to control delivery of insulin, and to perform functions. The functions include obtaining a number of blood glucose measurement values. The processor calculates a correction bolus dosage based on a latest blood glucose measurement value of the number of blood glucose measurement values. A rate of change of blood glucose values from the number of blood glucose measurement values over a period of time may be determined. A revised bolus dosage may be calculated using the determined rate of change and the latest blood glucose measurement value. A function may be applied to the correction bolus dosage and the revised bolus dosage. A final insulin value may be determined based on an output from the function.

Disclosed is a method that includes receiving a number of blood glucose measurement values over a period of time. A processor may determine a correction bolus dosage of insulin is required by a user based on an evaluation of the number of blood glucose measurement values. A final insulin value of the correction bolus dosage may be obtained based on an output of a function. The function utilizes a selected blood glucose measurement value of the number of blood glucose measurement values, a target blood glucose value of the user, and an insulin adjustment factor to generate the output of the function. An insulin bolus dosage may be set based on the obtained final insulin value, and delivery of insulin according to the set insulin bolus dosage may be actuated.

BRIEF DESCRIPTION OF THE DRAWINGS

FIG. 4 illustrates a flow chart of another example of a process for determining a dosage of a bolus injection for correcting a blood glucose value.

FIG. 5 illustrates a flow chart of an example subprocess for obtaining a final insulin value, such as the final insulin value of FIG. 4.

DETAILED DESCRIPTION

Various examples provide a method, a system, a device and a computer-readable medium for reducing risk of hypoglycemia by considering the glucose rate of change. For example, there may be the potential for a delay of several minutes, or tens of minutes, between an individual's actual blood glucose state relative to a blood glucose measurement value output by a CGM and when the patient will administer a bolus injection based on the blood glucose measurement value output by the CGM. In the disclosed examples, the delay between an individual's actual blood glucose state and when the patient bolus may be considered to optimize treatment. For example, a current blood glucose value received from a CGM may be projected forward assuming a constant rate of change for some number of minutes. This projected blood glucose value may be used in the calculation of a bolus determination (both time and amount).

An example provides a process that may be used with any additional algorithms or computer applications that manage blood glucose levels and insulin therapy. Such algorithms may be referred to as an "artificial pancreas" algorithm-based system, or more generally, an artificial pancreas (AP) application, that provides automatic delivery of an insulin based on a blood glucose sensor input, such as that received from a CGM or the like. In an example, the artificial pancreas (AP) application when executed by a processor may enable a system to monitor a user's glucose values, determine an appropriate level of insulin for the user based on the monitored glucose values (e.g., blood glucose concentrations or blood glucose measurement values) and other information, such as user-provided information, such as carbohydrate intake, exercise times, meal times or the like, and take actions to maintain a user's blood glucose value within an appropriate range. The appropriate blood glucose value range may be considered a target blood glucose value of the particular user. For example, a target blood glucose value may be acceptable if it falls within the range of 80 mg/dL to 120 mg/dL, which is a range satisfying the clinical standard of care for treatment of diabetes. However, an AP application as described herein may be able to establish a target blood glucose value more precisely and may set the target blood glucose value at, for example, 110 mg/dL, or the like. As described in more detail with reference to the examples of FIGS. 1-7, the AP application may utilize the monitored blood glucose values and other information to generate and send a command to a medical device including, for example, a pump, to control delivery of a bolus dose of insulin to the user, change the amount or timing of future doses, as well as to control other functions.

Figure 1:
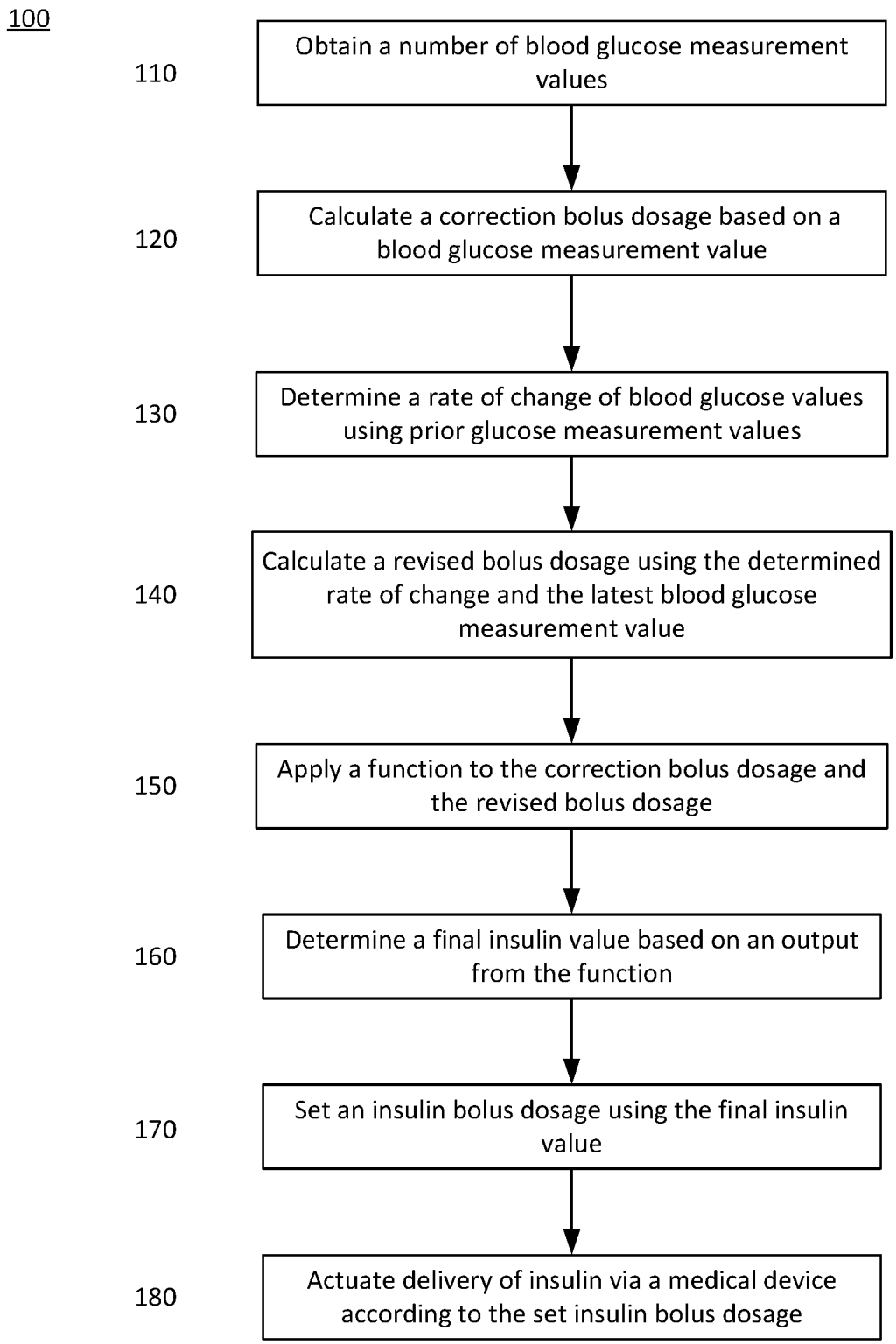
FIG. 1 shows a flow chart of an example process for determining a dosage of a bolus injection for correcting a blood glucose level.

FIG. 1 shows a flow chart of a process for determining a dosage of a bolus injection for correcting a blood glucose level. The process 100 may be implemented by programming code that is executed by a processor. For example, a processor when executing the programming code is operable to perform various functions. The various functions may include obtaining a number of blood glucose measurement values (110). For example, the number of blood glucose measurement values may be received over a period of time from a CGM or another device via a wireless signal (not shown in this example—hardware elements and system elements are described in more detail with reference to the example of FIG. 2). The period of time may be approximately every 5 minutes, every minute, or some other increment of time. In addition, an individual blood glucose measurement value of the number of blood glucose measurement values may be received very shortly, for example, almost instantaneously, after being measured, or may be delivered in a batch of two or more, or the like. The processor may process each of the number of blood glucose measurement values. Based on a blood glucose measurement value of the number of blood glucose measurement values, a correction bolus dosage may be calculated (120). For example, the blood glucose measurement value of the number of blood glucose measurement values used to calculate the correction bolus dosage may be a latest blood glucose measurement value. In this example, the latest blood glucose measurement value is the last blood glucose measurement value received by the processor may be the latest blood glucose measurement value. Alternatively, any of the number of blood glucose measurement values may be selected for use in the calculation of the correction bolus dosage.

$$\text{Correction Bolus Dosage} = \left(\frac{CGM - \text{target}}{ISF}\right) * IAF \qquad \text{Eq. 1}$$

A correction bolus dosage, as shown in Equation (Eq.) 1, may be calculated by determining a difference between the latest (or a selected) blood glucose measurement value and a target blood glucose value. The target blood glucose value may be considered the standard of care for a particular patient, standard of care for a large population of diabetics, or the desired glucose concentration preference for a particular patient. In some examples, in order to account for a particular user's capability to process insulin, an insulin sensitivity factor (ISF) may be applied (e.g. through multiplication, subtraction, division and/or other mathematical operation) to the determined difference to provide a personalized insulin value. In Eq. 1, ISF is a divisor of the difference between the latest blood glucose measurement value and a target blood glucose value and may be considered a parameter indicative of how much a user's measured blood glucose value drops per unit of insulin. In an example, ISF may be personalized for each user and is calculated from clinical values of the respective user determined based on user's diabetes (or other illness) treatment plan.

The personalized insulin value (i.e., ((CGM-target)/ISF)) may be further modified by applying an insulin adjustment factor (IAF) to the personalized insulin value to generate the correction bolus dosage. In an example, the range of values for IAF may be from approximately 0.30 to approximately 0.70. Of course, other ranges for the IAF may be used, such as 0.25-0.65, or the like. In some examples, the correction bolus dosage may be constrained at the upper boundary by a recommended bolus dosage modified by the IAF proportional to a trajectory of the number of blood glucose measurement values and another constraint may be that the recommended bolus is not more than is required to get the target blood glucose if the blood glucose trajectory is substantially constant for approximately 25 minutes (i.e., 5 cycles of blood glucose measurements by a CGM).

A rate of change (RoC) of blood glucose values may be determined from the number of blood glucose measurement values over the period of time (130). For example, the rate of change of the blood glucose measurement values may be derived from the slope. In other examples, a function fitted to a plot of each respective blood glucose measurement value over time may be determined and used to determine a rate of change. Alternatively, the rate of change of blood glucose value may be directly measured by a CGM.

At 140, the processor may use the determined rate of change and the latest blood glucose measurement value to calculate a revised bolus dosage. The rate of change may be multiplied by a time parameter to that will be used determine a modified latest blood glucose measurement value. For example, the processor may access a table of time parameters stored in memory. A time parameter may be selected from the table based on a predicted user response time to a dose of insulin, such as one unit of insulin, two units of insulin, or the like. The time parameter may be applied (e.g., as a multiplier) to the determined rate of change to generate a projected blood glucose measurement value (i.e., (RoC)× T=projected blood glucose measurement value). The latest blood glucose measurement value may be obtained by the processor using a latest blood glucose measurement and the projected blood glucose measurement value. For example, the processor may obtain the latest blood glucose measurement value from a memory coupled to the processor, a CGM, or via another external device, such as smart accessory device. The projected blood glucose measurement value may be added to the latest blood glucose measurement (CGM) value (e.g., CGM+(RoC)×T) to obtain a modified latest blood glucose measurement value. The time parameter T may be in minutes, such as 5 minutes, 15 minutes, 16 minutes, 25 minutes, or the like. The processor may retrieve a target blood glucose value (i.e., Target) of the user from a memory coupled to the processor. The difference between the target blood glucose value and the modified latest blood glucose measurement value may be determined. An insulin sensitivity factor (ISF) may be applied (as a divisor or fractional multiplier) to the determined difference to produce a revised bolus dosage as shown in the equation (Eq. 2) below, which may be implemented in programming code.

$$\text{Revised Bolus Dosage} = (CGM + RoC \times T) - \text{Target}/ISF \qquad \text{Eq. 2}$$

A function may be applied to the correction bolus dosage and the revised bolus dosage (150). The function may be, for example, a minimum function that is operable to find a minimum value of the inputs to the function as shown in equation 3 (Eq. 3).

$$\text{output} = \min(\text{correction bolus dosage, revised bolus dosage})$$

In this example, the inputs to the minimum function may be the correction bolus dosage and the revised bolus dosage, and, at 160, an output from the function, such as that shown in Eq. 3, may be used to determine a final insulin value. The final insulin value may be a volume of insulin, an amount of insulin (in units of insulin), or the like.

The processor may determine the final insulin value and perform further processing. For example, the determined final insulin value may be used to set an insulin bolus dosage (170). In response to setting the insulin bolus dosage, the processor may actuate delivery of insulin according to the set insulin bolus dosage (180). As described with respect to a further example, the processor may actuate delivery of insulin according to the set insulin bolus dosage, for example, by outputting a signal indicating the set insulin bolus dosage to be received by a pump mechanism. The pump mechanism, in response to the received signal, may operate to deliver a bolus dosage according to the set insulin bolus dosage.

Figure 2:
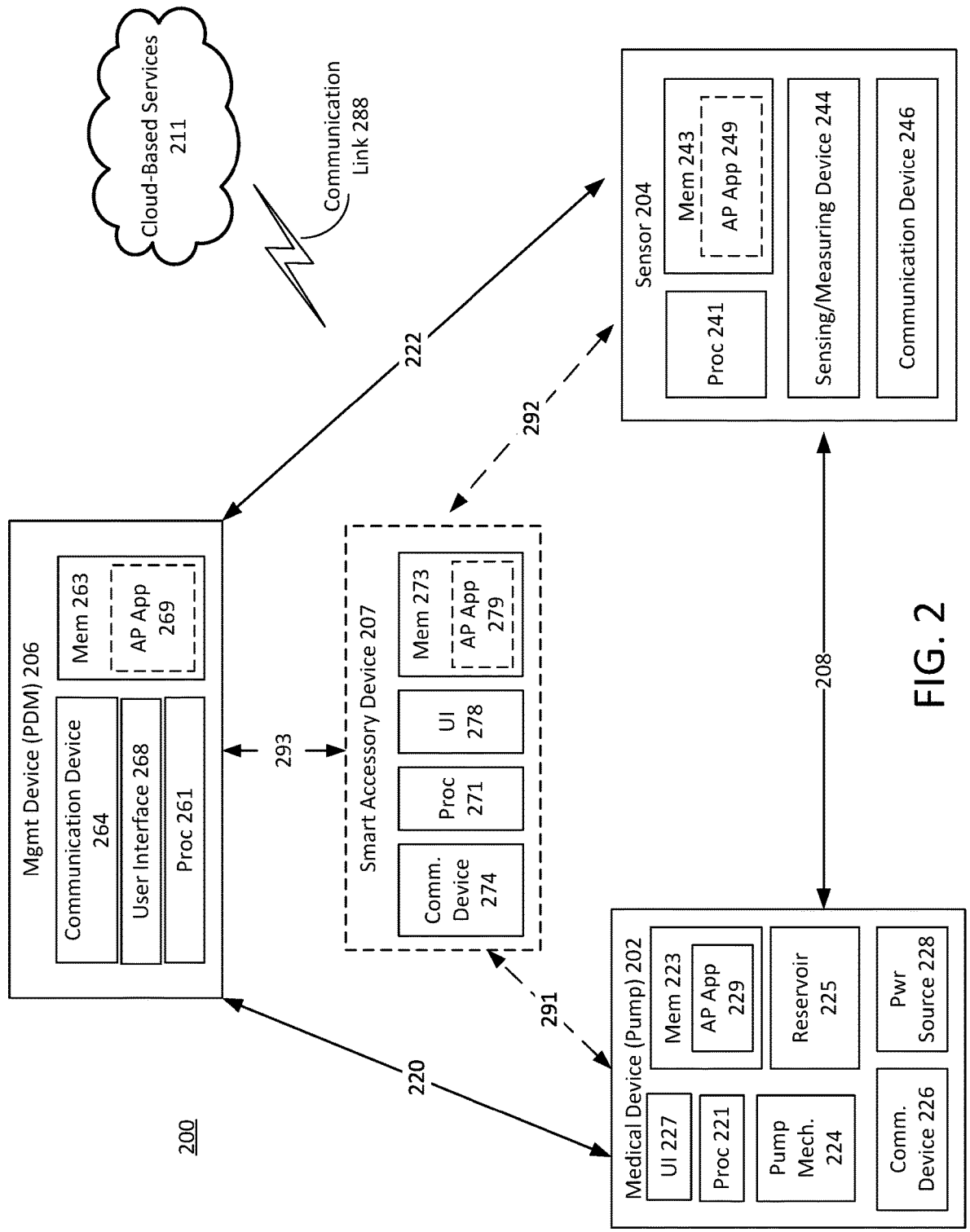
FIG. 2 illustrates a functional block diagram of drug delivery system suitable for implementing the example processes and techniques described herein.

It may be helpful to discuss an example of a drug delivery system that may implement the process example of FIG. 1. FIG. 2 illustrates an example of a drug delivery system 200.

The drug delivery system 200 may be operable to implement an AP application that includes functionality to determine a bolus dosage, output an indication of the determined bolus dosage to actuate delivery of the bolus of insulin based on the indication of the determined bolus dosage. The drug delivery system 200 may be an automated drug delivery system that may include a medical device (pump) 202, a sensor 204, and a management device (PDM) 206. The system 200, in an example, may also include a smart accessory device 207, which may communicate with the other components of system 200 either via a wired or wireless communication link.

In an example, the medical device 202 may be attached to the body of a user, such as a patient or diabetic, and may deliver any therapeutic agent, including any drug or medicine, such as insulin or the like, to a user. The medical device 202 may, for example, be a wearable device worn by the user. For example, the medical device 202 may be directly coupled to a user (e.g., directly attached to a body part and/or skin of the user via an adhesive or the like). In an example, a surface of the medical device 202 may include an adhesive to facilitate attachment to a user.

The medical device 202 may include a number of components to facilitate automated delivery of a drug (also referred to as a therapeutic agent) to the user. The medical device 202 may be operable to store the drug and to provide the drug to the user. The medical device 202 is often referred to as a pump, or an insulin pump, in reference to the operation of expelling a drug from the reservoir 225 for delivery to the user. While the examples refer to the reservoir 225 storing insulin, the reservoir 225 may be operable to store other drugs or therapeutic agents, such as morphine or the like, suitable for automated delivery.

In various examples, the medical device 202 may be an automated, wearable insulin delivery device. For example, the medical device 202 may include a reservoir 225 for storing the drug (such as insulin), a needle or cannula (not shown) for delivering the drug into the body of the user (which may be done subcutaneously, intraperitoneally, or intravenously), and a pump mechanism (mech.) 224, or other drive mechanism, for transferring the drug from the reservoir 225, through a needle or cannula (not shown), and into the user. The pump mechanism 224 may be fluidly coupled to reservoir 225, and communicatively coupled to the processor 221. The medical device 202 may also include a power source 228, such as a battery, a piezoelectric device, or the like, for supplying electrical power to the pump mechanism 224 and/or other components (such as the processor 221, memory 223, and the communication device 226) of the medical device 202. Although not shown, an electrical power supply for supplying electrical power may similarly be included in each of the sensor 204, the smart accessory device 207 and the management device (PDM) 206.

The blood glucose sensor 204 may be a device communicatively coupled to the processor 261 or 221 and may be operable to measure a blood glucose value at a predetermined time interval, such as every 5 minutes, or the like. The blood glucose sensor 204 may provide a number of blood glucose measurement values to the AP applications operating on the respective devices.

The medical device 202 may provide insulin the stored in reservoir 225 to the user based on information (e.g., blood glucose measurement values) provided by the sensor 204 and/or the management device (PDM) 206. For example, the medical device 202 may contain analog and/or digital circuitry that may be implemented as a processor 221 (or controller) for controlling the delivery of the drug or therapeutic agent. The circuitry used to implement the processor 221 may include discrete, specialized logic and/or components, an application-specific integrated circuit, a microcontroller or processor that executes software instructions, firmware, programming instructions or programming code (enabling, for example, the artificial pancreas application (AP App) 229 as well as the process examples of FIGS. 1 and 3) stored in memory 223, or any combination thereof. For example, the processor 221 may execute a control algorithm, such as an artificial pancreas application 229, and other programming code that may make the processor 221 operable to cause the pump to deliver doses of the drug or therapeutic agent to a user at predetermined intervals or as needed to bring blood glucose measurement values to a target blood glucose value. The size and/or timing of the doses may be programmed, for example, into an artificial pancreas application 229 by the user or by a third party (such as a health care provider, medical device manufacturer, or the like) using a wired or wireless link, such as 220, between the medical device 202 and a management device 206 or other device, such as a computing device at a healthcare provider facility. In an example, the pump or medical device 202 is communicatively coupled to the processor 261 of the management device via the wireless link 220 or via a wireless link, such as 291 from smart accessory device 207 or 208 from the sensor 204. The pump mechanism 224 of the medical device may be operable to receive an actuation signal from the processor 261, and in response to receiving the actuation signal, expel insulin from the reservoir 225 according to the set insulin bolus dosage.

The other devices in the system 200, such as management device 206, smart accessory device 207 and sensor 204, may also be operable to perform various functions including controlling the medical device 202. For example, the management device 206 may include a communication device 264, a processor 261, and a management device memory 263. The management device memory 263 may store an instance of the AP application 269 that includes programming code, that when executed by the processor 261 provides the process examples described with reference to the examples of FIGS. 1 and 3. The management device memory 263 may also store programming code for providing the process examples described with reference to the examples of FIGS. 1 and 3-7.

The smart accessory device 207 may be, for example, an Apple Watch®, other wearable smart device, including eyeglasses, provided by other manufacturers, a global positioning system-enabled wearable, a wearable fitness device, smart clothing, or the like. Similar to the management device 206, the smart accessory device 207 may also be operable to perform various functions including controlling the medical device 202. For example, the smart accessory device 207 may include a communication device 274, a processor 271, and a memory 273. The memory 273 may store an instance of the AP application 279 that includes programming code for providing the process examples described with reference to the examples of FIGS. 1 and 3-7. The memory 273 may also as store programming code and be operable to store data related to the AP application 279. The sensor 204 of system 200 may be a continuous glucose monitor (CGM) as described above, that may include a processor 241, a memory 243, a sensing or measuring device 244, and a communication device 246. The memory 243 may store an instance of an AP application 249 as well as other programming code and be operable to store data related to the AP application 249. The AP application 249 may also include programming code for providing the process examples described with reference to the examples of FIGS. 1 and 3-7.

Instructions for determining the delivery of the drug or therapeutic agent (e.g., as a bolus dosage) to the user (e.g., the size and/or timing of any doses of the drug or therapeutic agent) may originate locally by the medical device 202 or may originate remotely and be provided to the medical device 202. In an example of a local determination of drug or therapeutic agent delivery, programming instructions, such as an instance of the artificial pancreas application 229, stored in the memory 223 that is coupled to the medical device 202 may be used to make determinations by the medical device 202. In addition, the medical device 202 may be operable to communicate with the cloud-based services 211 via the communication device 226 and the communication link 288.

Alternatively, the remote instructions may be provided to the medical device 202 over a wired or wireless link by the management device (PDM) 206, which has a processor 261 that executes an instance of the artificial pancreas application 269, or the smart accessory device 207, which has a processor 271 that executes an instance of the artificial pancreas application 269 as well as other programming code for controlling various devices, such as the medical device 202, smart accessory device 207 and/or sensor 204. The medical device 202 may execute any received instructions (originating internally or from the management device 206) for the delivery of the drug or therapeutic agent to the user. In this way, the delivery of the drug or therapeutic agent to a user may be automated.

In various examples, the medical device 202 may communicate via a wireless link 220 with the management device 206. The management device 206 may be an electronic device such as, for example, a smart phone, a tablet, a dedicated diabetes therapy management device, or the like. The management device 206 may be a wearable wireless accessory device. The wireless links 208, 220, 222, 291, 292 and 293 may be any type of wireless link provided by any known wireless standard. As an example, the wireless links 208, 220, 222, 291, 292 and 293 may enable communications between the medical device 202, the management device 206 and sensor 204 based on, for example, Bluetooth®, Wi-Fi®, a near-field communication standard, a cellular standard, or any other wireless optical or radio-frequency protocol.

The sensor 204 may be a glucose sensor operable to measure blood glucose and output a blood glucose value or data that is representative of a blood glucose value. For example, the sensor 204 may be a glucose monitor or a continuous glucose monitor (CGM). The sensor 204 may include a processor 241, a memory 243, a sensing/measuring device 244, and communication device 246. The communication device 246 of sensor 204 may include one or more sensing elements, an electronic transmitter, receiver, and/or transceiver for communicating with the management device 206 over a wireless link 222 or with medical device 202 over the link 208. The sensing/measuring device 244 may include one or more sensing elements, such as a glucose measurement, heart rate monitor, or the like. The processor 241 may include discrete, specialized logic and/or components, an application-specific integrated circuit, a microcontroller or processor that executes software instructions, firmware, programming instructions stored in memory (such as memory 243), or any combination thereof. For example, the memory 243 may store an instance of an AP application 249 that is executable by the processor 241.

Although the sensor 204 is depicted as separate from the medical device 202, in various examples, the sensor 204 and medical device 202 may be incorporated into the same unit. That is, in various examples, the sensor 204 may be a part of the medical device 202 and contained within the same housing of the medical device 202 (e.g., the sensor 204 may be positioned within or embedded within the medical device 202). Glucose monitoring data (e.g., measured blood glucose values) determined by the sensor 204 may be provided to the medical device 202, smart accessory device 207 and/or the management device 206 and may be used to determine a bolus dosage of insulin for automated delivery of insulin by the medical device 202.

The sensor 204 may also be coupled to the user by, for example, adhesive or the like and may provide information or data on one or more medical conditions and/or physical attributes of the user. The information or data provided by the sensor 204 may be used to adjust drug delivery operations of the medical device 202.

In an example, the management device 206 may be a personal diabetes manager. The management device 206 may be used to program or adjust operation of the medical device 202 and/or the sensor 204. The management device 206 may be any portable electronic device including, for example, a dedicated controller, such as processor 261, a smartphone, or a tablet. In an example, the management device (PDM) 206 may include a processor 261, a management device management device memory 263, and a communication device 264. The management device 206 may contain analog and/or digital circuitry that may be implemented as a processor 261 (or controller) for executing processes to manage a user's blood glucose levels and for controlling the delivery of the drug or therapeutic agent to the user. The processor 261 may also be operable to execute programming code stored in the management device management device memory 263. For example, the management device management device memory 263 may be operable to store an artificial pancreas application 269 that may be executed by the processor 261. The processor 261 may when executing the artificial pancreas application 269 may be operable to perform various functions, such as those described with respect to the examples in FIGS. 1 and 3. The communication device 264 may be a receiver, a transmitter, or a transceiver that operates according to one or more radio-frequency protocols. For example, the communication device 264 may include a cellular transceiver and a Bluetooth transceiver that enables the management device 206 to communicate with a data network via the cellular transceiver and with the sensor 204 and the medical device 202. The respective transceivers of communication device 264 may be operable to transmit signals containing information useable by or generated by the AP application or the like. The communication devices 226, 246 and 276 of respective medical device 202, sensor 204 and smart accessory device 207 may also be operable to transmit signals containing information useable by or generated by the AP application or the like.

The medical device 202 may communicate with the sensor 204 over a wireless link 208 and may communicate with the management device 206 over a wireless link 220. The sensor 204 and the management device 206 may communicate over a wireless link 222. The smart accessory device 207, when present, may communicate with the medical device 202, the sensor 204 and the management device 206 over wireless links 291, 292 and 293, respectively. The wireless links 208, 220, 222, 291, 292 and 293 may be any type of wireless link operating using known wireless standards or proprietary standards. As an example, the wireless links 208, 220, 222, 291, 292 and 293 may provide communication links based on Bluetooth®, Wi-Fi, a near-field communication standard, a cellular standard, or any other wireless protocol via the respective communication devices 226, 246 and 264. In some examples, the medical device 202 and/or the management device 206 may include a user interface 227 and 268, respectively, such as a keypad, a touchscreen display, levers, buttons, a microphone, a speaker, a display, or the like, that is operable to allow a user to enter information and allow the management device to output information for presentation to the user.

In various examples, the drug delivery system 200 may be an insulin drug delivery system. In various examples, the medical device 202 may be the OmniPod® (Insulet Corporation, Billerica, Ma.) insulin delivery device as described in U.S. Pat. Nos. 7,303,549, 7,137,964, or 6,740,059, each of which is incorporated herein by reference in its entirety.

In various examples, the drug delivery system 200 may implement the artificial pancreas (AP) algorithm (and/or provide AP functionality) to govern or control automated delivery of insulin to a user (e.g., to maintain euglycemia—a normal level of glucose in the blood). The AP application may be implemented by the medical device 202 and/or the sensor 204. The AP application may be used to determine the times and dosages of insulin delivery. In various examples, the AP application may determine the times and dosages for delivery based on information known about the user, such as the user's sex, age, weight, or height, and/or on information gathered about a physical attribute or condition of the user (e.g., from the sensor 204). For example, the AP application may determine an appropriate delivery of insulin based on glucose level monitoring of the user through the sensor 204. The AP application may also allow the user to adjust insulin delivery. For example, the AP application may allow the user to issue (e.g., via an input) commands to the medical device 202, such as a command to deliver an insulin bolus. In some examples, different functions of the AP application may be distributed among two or more of the management device 206, the medical device (pump) 202 or the sensor 204. In other examples, the different functions of the AP application may be performed by one device, such the management device 206, the medical device (pump) 202 or the sensor 204. In various examples, the drug delivery system 200 may operate according to or may include features or functionalities of the drug delivery systems described in U.S. patent application Ser. No. 15/359,187, filed Nov. 22, 2016, which is incorporated herein by reference in its entirety.

As described herein, the drug delivery system 200 or any component thereof, such as the medical device may be considered to provide AP functionality or to implement an AP application. Accordingly, references to the AP application (e.g., functionality, operations, or capabilities thereof) are made for convenience and may refer to and/or include operations and/or functionalities of the drug delivery system 200 or any constituent component thereof (e.g., the medical device 202 and/or the management device 206). The drug delivery system 200—for example, as an insulin delivery system implementing an AP application—may be considered to be a drug delivery system or an AP application-based delivery system that uses sensor inputs (e.g., data collected by the sensor 204).

In an example, one or more of the devices, 202, 204, 206 or 207 may be operable to communicate via a wireless communication link 288 with cloud-based services 211. The cloud-based services 211 may utilize servers and data storage (not shown). The communication link 288 may be a cellular link, a Wi-Fi link, a Bluetooth link, or a combination thereof, that is established between the respective devices 202, 204, 206 or 207 of system 200. The data storage provided by the cloud-based services 211 may store anonymized data, such as user weight, blood glucose measurements, age, meal carbohydrate information, or the like. In addition, the cloud-based services 211 may process the anonymized data from multiple users to provide generalized information related to the various parameters used by the AP application. For example, an age-based general target blood glucose value may be derived from the anonymized data, which may be helpful when a user first begins using a system such as 200. The cloud-based services 211 may also provide processing services for the system 200, such as performing the process 100 in the example of FIG. 2 or additional processes, such as that described below with reference to FIG. 3.

In an example, the device 202 includes a communication device 264, which as described above may be a receiver, a transmitter, or a transceiver that operates according to one or more radio-frequency protocols, such as Bluetooth, Wi-Fi, a near-field communication standard, a cellular standard, that may enable the respective device to communicate with the cloud-based services 211. For example, outputs from the sensor 204 or the medical device (pump) 202 may be transmitted to the cloud-based services 211 for storage or processing via the transceivers of communication device 264. Similarly, medical device 202, management device 206 and sensor 204 may be operable to communicate with the cloud-based services 211 via the communication link 288.

In an example, the respective receiver or transceiver of each respective device, 202, 206 or 207, may be operable to receive signals containing respective blood glucose measurement values of the number of blood glucose measurement values that may be transmitted by the sensor 204. The respective processor of each respective device 202, 206 or 207 may be operable to store each of the respective blood glucose measurement values in a respective memory, such as 223, 263 or 273. The respective blood glucose measurement values may be stored as data related to the artificial pancreas algorithm, such as 229, 249, 269 or 279. In a further example, the AP application operating on any of the management device 206, the smart accessory device 207, or sensor 204 may be operable to transmit, via a transceiver implemented by a respective communication device, 264, 274, 246, a control signal for receipt by a medical device. In the example, the control signal may indicate an amount of insulin to be expelled by the medical device 202.

Figure 3:
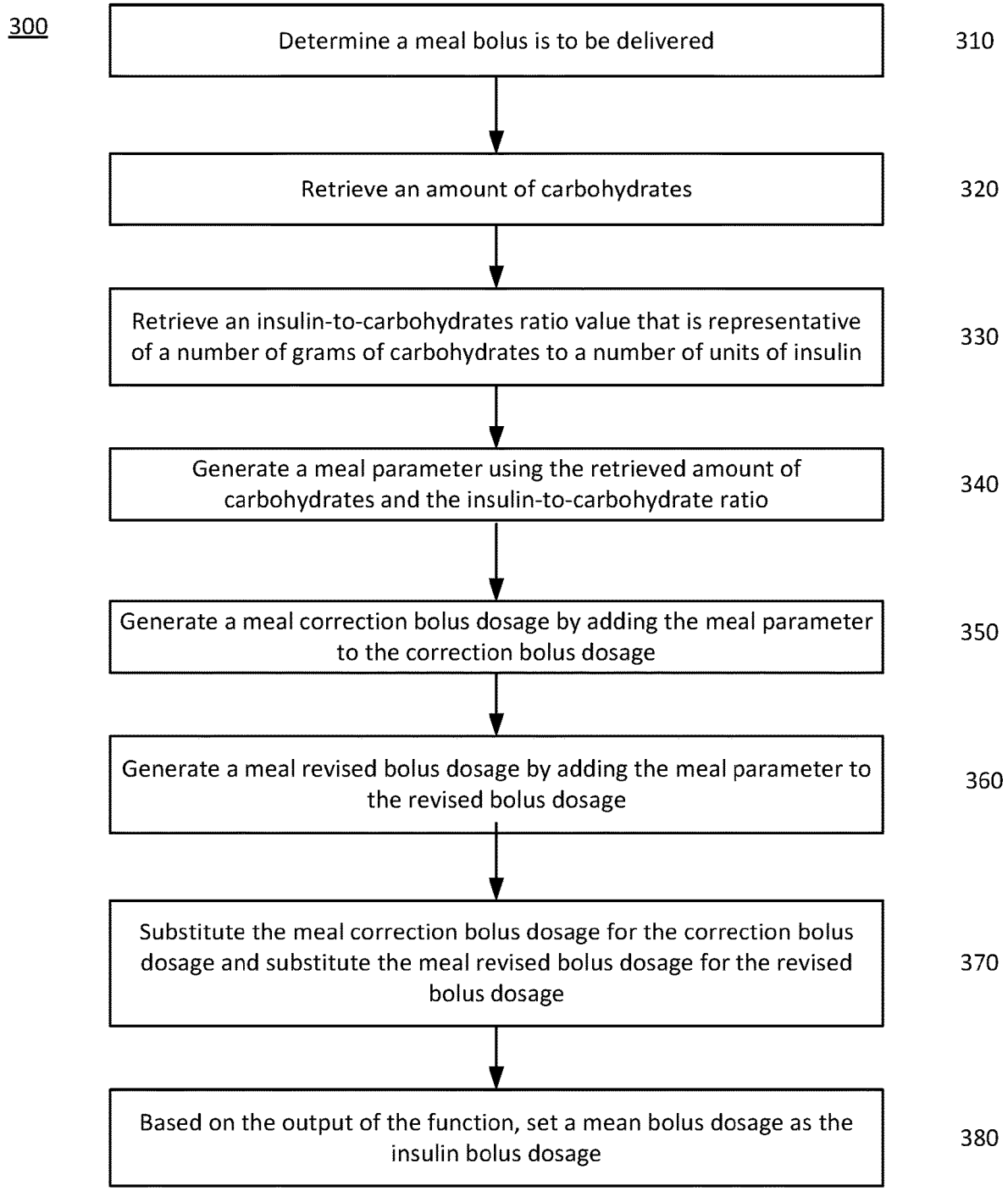
FIG. 3 illustrates a flow chart of an example process for determining a bolus dosage that is to be administered in response to consumption of a meal.

Various operational scenarios and examples of processes performed by the system 200 are described herein. For example, the system 200 may be operable to implement the process example of FIG. 1. In addition, the system 200 may be operable to implement a process that accounts for a meal correction bolus. FIG. 3 illustrates a process example for determining a dosage of a meal correction bolus. The process 300 may be considered a specific implementation of the process 100 of FIG. 1 for use when a meal is consumed, and a meal correction bolus is to be administered to the user. In the example process 300, a processor, such as 221 or 261 of the example in FIG. 2, may be operable to execute programming code to perform the different functions including a determination of whether an indication of a meal bolus is to be output, or an indication of a correction bolus is to be output. The process 300 is similar to the process 100 but with an added parameter that accounts for an amount of carbohydrates consumed by a user and the user's insulin-to-carbohydrate ratio value. In the process 300, a processor, such as 221 or 261, may determine, at 310, that a meal bolus is to be delivered. The consumption of carbohydrates by a user acts to raise the level of glucose in the user's blood. A meal bolus may be delivered to counteract the effects of the ingestion of carbohydrates. For example, a user may be about to ingest or may have finished, a meal and may provide an input via a user interface, such as 268, 227 or 278 to either the PDM 206, medical device 202 or the smart accessory device 278 of FIG. 2 indicating the impending or completed meal. Indications of the impending or completed meal may be used to determine that a meal bolus is to be delivered. For example, a processor may receive information indicating that a meal bolus may be needed, such as a meal bolus request input from a user, a scheduled meal time, a calendar message, a GPS/Wi-Fi location determination, or the like. Typically, when a meal is consumed a meal bolus is administered to counteract the effects of the additional carbohydrates.

At 320, in response to determining a meal bolus is to be delivered, an amount of carbohydrates may be retrieved. The amount of carbohydrates may be an expected amount (a value provided before eating) of carbohydrates to be consumed, an actual amount of carbohydrates consumed (from a nutrition label on a package, or the like), an estimated amount (a value provided after eating) of carbohydrates consumed, or the like, that are input into the system 200 by a user or someone else familiar (e.g., a dietician, a healthcare provider) with the meal being consumed by the user. The amount of carbohydrates may also be received from the cloud-based services 211 in response to a list of foods and approximate portion sizes input by a user, a name of a meal provided by a restaurant that participates with services provided by the cloud-based services 211, or the like.

At 330, the processor may retrieve an insulin-to-carbohydrates ratio (ICR) value that is representative of a number of grams of carbohydrates to a number of units of insulin (e.g., grams per unit of insulin). The ICR value may be stored in a memory, such as 223, 243, 263 or 273 of the respective devices 202, 204, 206 and 207 of FIG. 2. The ICR may be updated according to a setting in the AP application. For example, the ICR may be updated with each measurement of blood glucose reported by the sensor 204 to the AP application or may be updated daily using a number of blood glucose measurements by a respective processor executing the AP application in any one of medical device 202, management device 206 or smart accessory device 207. The AP application may use the retrieved amount of carbohydrates and the insulin-to-carbohydrate ratio value to generate a meal parameter (340). For example, the AP application may be operable to calculate the meal parameter using an equation such as an amount of carbohydrates (CHO) in grams, for example, divided by the ICR to arrive at a meal parameter having a number of units of insulin as a value.

The AP application executed by the processor, at 350, may generate a meal correction bolus dosage for output by an insulin pump device, such as the medical device 202 of FIG. 2, by determining the difference of the blood glucose measurement value from the CGM and the target blood glucose value divided by the ISF, summing the meal parameter and the difference, and multiplying the sum of the meal parameter and the difference with an IAF for the user as shown in Equation 4 below.

$$\text{Meal Correction Bolus Dosage} = \left(\left(\frac{CHO}{ICR}\right) + \frac{(CGM - \text{Target})}{ISF}\right) * IAF \quad \text{Eq. 4}$$

The AP application executed by the processor may generate a meal revised bolus dosage by adding the meal parameter to the revised bolus dosage (360). For example, the AP application executed by the processor may generate a meal revised bolus dosage for output by an insulin pump device, such as the medical device 202 of FIG. 2, by adding the meal parameter to the correction bolus dosage (as described above with reference to FIG. 1) as shown in Equation 5 below.

$$\text{Meal Revised Bolus Dosage} = \left(\left(\frac{CHO}{ICR}\right) + \frac{(CGM + RoC*T - \text{Target})}{ISF}\right) \quad \text{Eq. 5}$$

The function in the process 100, step 150, is applied to determine a meal bolus dosage, except the meal correction bolus dosage may be substituted for the correction bolus dosage and the meal revised bolus dosage may be substituted for the revised bolus dosage to determine a minimum value as shown in Eq. 6 below (370).

$$\text{Output=min(meal correction bolus dosage, meal revised bolus dosage)} \quad \text{Eq. 6}$$

Based on the meal bolus dosage output from the function in Eq. 6, the insulin bolus dosage set equal to the meal bolus dosage (380). In response to control signals generated according the set insulin bolus dosage by an AP application, an insulin bolus may be administered by the medical device 202 to a user.

In the foregoing examples, the bolus dosage calculations for either a correction bolus or a meal correction bolus are described as be included with the programming code of the AP application. However, the foregoing examples may be implemented as add-on programing for use in applications offered by different service providers that deliver functions similar to the AP application described herein.

Additional methods of calculating an insulin bolus are also disclosed. For example, processes that include specific modifications to a generalized process are disclosed. An example of a generalized process is shown in FIG. 4. The process 400 of FIG. 4 includes, at 415 receiving a number of blood glucose measurement values over a period of time. As mentioned, the number of blood glucose measurement values may be made by a CGM over a period of time. For example, a sensor, such as 204, may measure a user's blood glucose every 5 minutes for several days (e.g., until the sensor's power supply is depleted) and provide the results to an AP application executing on a medical device or a management device.

The processor on a medical device or a management device may determine a correction bolus dosage of insulin is required by a user based on an evaluation of the number of blood glucose measurement values (415). In the example, the medical device processor may determine that a correction bolus dosage of insulin is required by a user based on an evaluation of the number of blood glucose measurement values (425). For example, the processor may be operable to access information from a data storage, which may be, for example, a memory coupled to the processor, other devices in the system, such as the sensor, a medical device, a smart accessory device, a management device, a cloud-based service, or the like. Alternatively, or in addition, the processor may be operable to calculate or derive the information useable in the determination of the correction bolus dosage. In the example, the processor may apply a function to the selected blood glucose measurement value of the number of blood glucose measurement values, the target blood glucose value of the user, and the insulin adjustment factor. At 435, the processor may obtain a final insulin value of the correction bolus dosage based on an output of the function. The final insulin value may be a volume of insulin, an amount of insulin (in units of insulin), or the like that is to be used to determine an insulin bolus dosage. For example, an insulin bolus dosage may be set based on the obtained final insulin value (445). At 455, delivery of insulin may be actuated according to the set insulin bolus dosage. For example, the processor 221 may generate a control signal that is applied to the pump mechanism 224 to expel an amount of insulin according to the set insulin bolus dosage.

The step of obtaining a final insulin value at 435 may be performed using different process examples. FIG. 5 illustrates a flow chart of an example subprocess for obtaining the final insulin value may be completed by a processor applying a process. The process 500 may be implemented via programming code, for example, as part of the AP application, that enables a processor to calculate a difference between the selected blood glucose measurement value and the target blood glucose value of the user (510). The processor may determine which of the calculated difference or a maximum correction blood glucose value is a lower blood glucose value (520). At 530, when the lower blood glucose value is determined, an insulin adjustment factor may be applied to the lower blood glucose value. A result of the applying the insulin adjustment factor to the lower blood glucose value may be output (540).

Figure 6A:
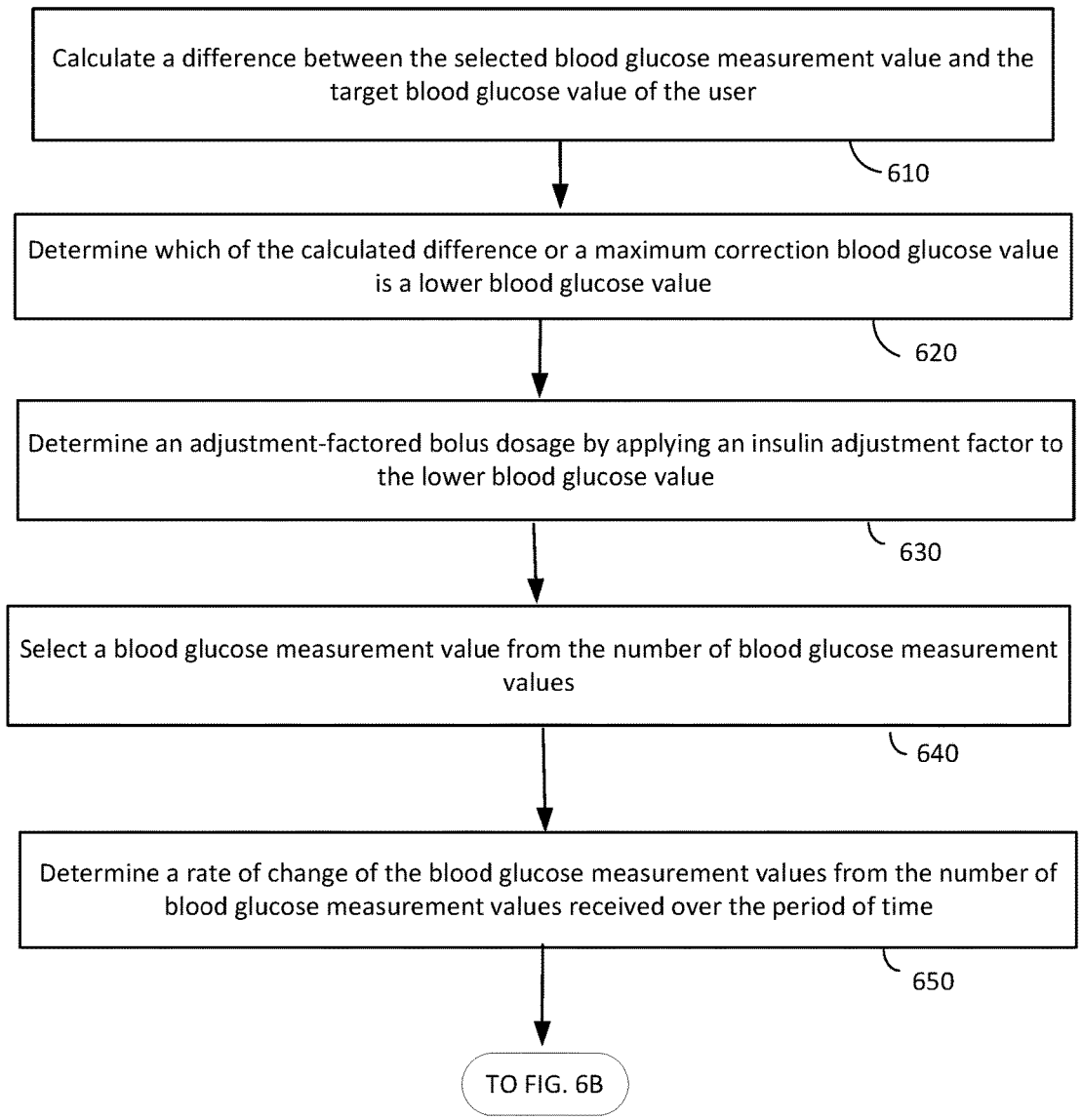
FIGS. 6A and 6B illustrate a flow chart of another example subprocess for obtaining a final insulin value.
Figure 6B:
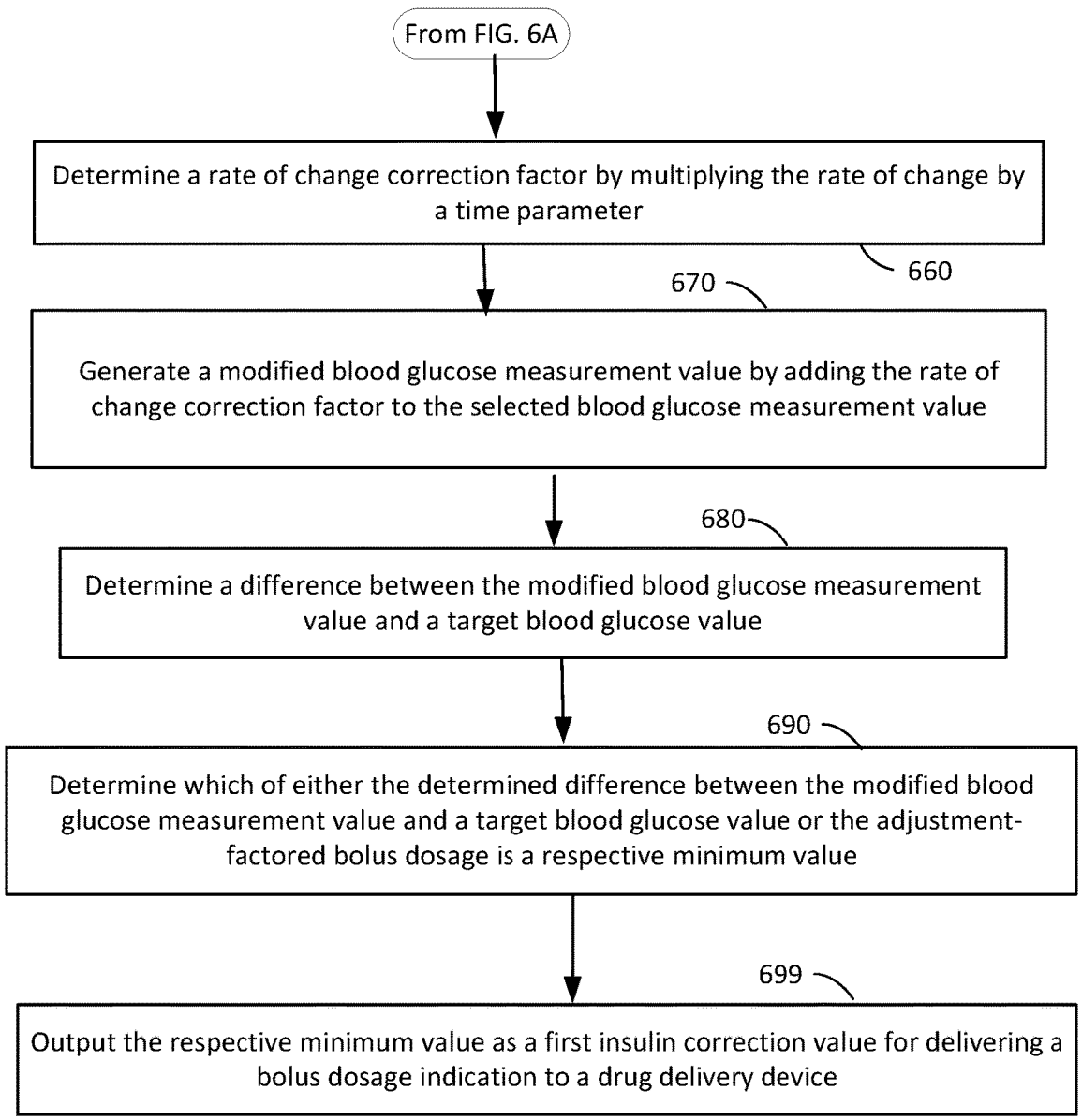

Alternatively, in another example shown in FIGS. 6A and 6B, the step of obtaining a final insulin value at 435 may be performed by a processor executing programming code that causes the processor to be operable to perform the functions of process 600. For example, at 610, the processor may calculate a difference between the selected blood glucose measurement and the target blood glucose value of the user. A determination may be made which of the calculated difference or a maximum correction blood glucose value is a lower blood glucose value (620). The maximum correction blood glucose value may be a fixed clinical medical value, such as 100 mg/dL, modifiable based on user preferences from 0 to 300 mg/dL, implied based on user's maximum bolus setting and insulin sensitivity factor clinical parameters as seen in Equation 7 below, or the like.

$$\text{Maximum Correction blood glucose} = \frac{\text{User's Maximum Bolus Setting}}{ISF} \quad \text{Eq. 7}$$

In other examples, the maximum correction blood glucose value may be specific to the particular user. For example, the maximum correction blood glucose value may be determined based on user history of administered dosages and analysis of the user's response to each respective administered dosage. The determination, at 620, may be made using a direct comparison of the respective values of the difference and the maximum correction blood glucose value, or by applying a bias weighting (e.g., a percentage such as 80/20, 60/40, a direct bias weighting, such as 0.2, or the like) to the difference, the maximum correction blood glucose value, or both.

At 630, an adjustment-factored bolus dosage may be determined by applying an insulin adjustment factor (such as IAF shown in the examples that utilize Eq. 1 or Eq. 4 above) to the lower blood glucose value determined in 620.

A blood glucose measurement value may be selected from the number of blood glucose measurement values (640). The processor may select the blood glucose measurement value based on a number of factors. For example, the selected blood glucose measurement value may be the blood glucose measurement value most recently received (i.e., the latest blood glucose measurement value) from a CGM or input into a medical device, for example, by a user, one of a blood glucose measurement value received with the past 15 minutes, 25 minutes or some other time period, or the like.

At 650, a rate of change of the blood glucose measurement values may be determined from the number of blood glucose measurement values received over the period of time. The rate of change may be determined using a number of known methods. Moving to FIG. 6B, a rate of change correction factor may be determined by multiplying the rate of change determined at 650 by a time parameter (660). Units for the rate of change of the blood glucose measurement values may be milligrams/deciliter per unit of time. A time parameter, such as T in Eq. 2, may be a time value represented in units of time such as minutes (e.g. 5, 10, 15 or 25 minutes), or the like. Of course, conversion of the time units to seconds or fractions of hours may also be used. In the example, the processor executing the programming code may generate a modified blood glucose measurement value by adding the rate of change correction factor to the selected blood glucose measurement value (670). The processor executing the programming code may determine, at 680, a difference between the modified blood glucose measurement value and a target blood glucose value. At 690, the processor executing the programming code may determine which of either the determined difference between the modified blood glucose measurement value and a target blood glucose value or the adjustment-factored bolus dosage is a respective minimum value. The processor may output the respective minimum value as a first insulin correction value for delivering a bolus dosage indication to a drug delivery device (699).

Figure 7:
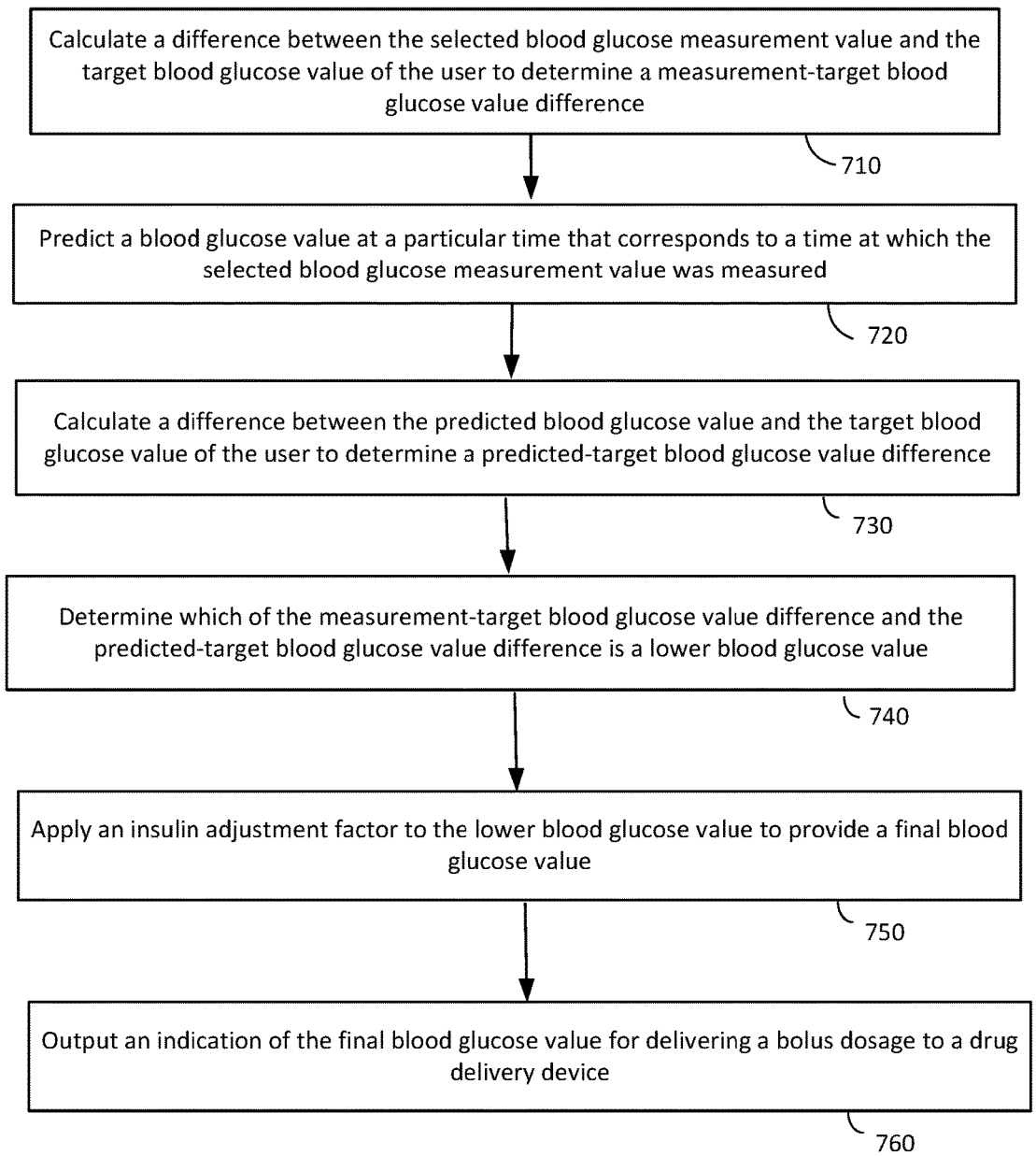
FIG. 7 illustrates a flow chart of a further example subprocess for obtaining a final insulin value.

In another alternative, FIG. 7 illustrates a flow chart of a further example subprocess for obtaining a final insulin value. As shown in the example of FIG. 7, the step of obtaining a final insulin value at 435 may be performed by a processor executing programming code that causes the processor to be operable to perform the functions of process 700. For example, at 710, the processor may calculate a difference between the selected blood glucose measurement value and the target blood glucose value of the user to determine a measurement-target blood glucose value differences. A prediction of a blood glucose value at a particular time that corresponds to a time at which the selected blood glucose measurement value was measured may be made by a processor at 720. The prediction may be based on prior user blood glucose measurements, a history of administered doses of insulin, or the like. A difference between the predicted blood glucose value and the target blood glucose value of the user may be calculated to determine a predicted-target blood glucose value difference (730). The processor executing the programming code may be operable to determine which of the measurement-target blood glucose value difference and the predicted-target blood glucose value difference is a lower blood glucose value (740). This may be determined using various methods such as a direct comparison or other process. In response to determine which the respective values is the lower blood glucose value in 740, an insulin adjustment factor may be applied to the lower blood glucose value to provide a final blood glucose value (750). For example, the lower blood glucose value may be multiplied or divided by the insulin adjustment factor or some other operation or function may apply the insulin adjustment factor to the lower blood glucose value.

In response to determining the final blood glucose value, a processor may, at 760, output an indication of the final blood glucose value for delivering a bolus dosage to a drug delivery device. The outputted indication may be used to generate a signal that is applied to a pump mechanism, such as 224 of FIG. 2, to deliver a bolus dosage to the drug delivery device.

The techniques described herein for providing safety constraints for a drug delivery system (e.g., the system 200 or any component thereof) may be implemented in hardware, software, or any combination thereof. For example, the system 200 or any component thereof may be implemented in hardware, software, or any combination thereof. Software related implementations of the techniques described herein may include, but are not limited to, firmware, application specific software, or any other type of computer readable instructions that may be executed by one or more processors. Hardware related implementations of the techniques described herein may include, but are not limited to, integrated circuits (ICs), application specific ICs (ASICs), field programmable arrays (FPGAs), and/or programmable logic devices (PLDs). In some embodiments, the techniques described herein, and/or any system or constituent component described herein may be implemented with a processor executing computer readable instructions stored on one or more memory components.

Some embodiments of the disclosed device may be implemented, for example, using a storage medium, a computer-readable medium, or an article of manufacture which may store an instruction or a set of instructions that, if executed by a machine (i.e., processor or microcontroller), may cause the machine to perform a method and/or operation in accordance with embodiments of the disclosure. Such a machine may include, for example, any suitable processing platform, computing platform, computing device, processing device, computing system, processing system, computer, processor, or the like, and may be implemented using any suitable combination of hardware and/or software. The computer-readable medium or article may include, for example, any suitable type of memory unit, memory, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, programming code, and the like, implemented using any suitable high-level, low-level, object-oriented, visual, compiled and/or interpreted programming language. The non-transitory computer readable medium embodied programming code may cause a processor when executing the programming code to perform functions, such as those described herein.

Certain examples of the present disclosure were described above. It is, however, expressly noted that the present disclosure is not limited to those examples, but rather the intention is that additions and modifications to what was expressly described herein are also included within the scope of the disclosed examples. Moreover, it is to be understood that the features of the various examples described herein were not mutually exclusive and may exist in various combinations and permutations, even if such combinations or permutations were not made express herein, without departing from the spirit and scope of the disclosed examples. In fact, variations, modifications, and other implementations of what was described herein will occur to those of ordinary skill in the art without departing from the spirit and the scope of the disclosed examples. As such, the disclosed examples are not to be defined only by the preceding illustrative description.

Program aspects of the technology may be thought of as "products" or "articles of manufacture" typically in the form of executable code and/or associated data that is carried on or embodied in a type of machine readable medium. Storage type media include any or all of the tangible memory of the computers, processors or the like, or associated modules thereof, such as various semiconductor memories, tape drives, disk drives and the like, which may provide non-transitory storage at any time for the software programming. It is emphasized that the Abstract of the Disclosure is provided to allow a reader to quickly ascertain the nature of the technical disclosure. It is submitted with the understanding that it will not be used to interpret or limit the scope or meaning of the claims. In addition, in the foregoing Detailed Description, various features are grouped together in a single example for streamlining the disclosure. This method of disclosure is not to be interpreted as reflecting an intention that the claimed examples require more features than are expressly recited in each claim. Rather, as the following claims reflect, inventive subject matter lies in less than all features of a single disclosed example. Thus, the following claims are hereby incorporated into the Detailed Description, with each claim standing on its own as a separate example. In the appended claims, the terms "including" and "in which" are used as the plain-English equivalents of the respective terms "comprising" and "wherein," respectively. Moreover, the terms "first," "second," "third," and so forth, are used merely as labels and are not intended to impose numerical requirements on their objects.

The foregoing description of example embodiments has been presented for the purposes of illustration and description. It is not intended to be exhaustive or to limit the present disclosure to the precise forms disclosed. Many modifications and variations are possible in light of this disclosure. It is intended that the scope of the present disclosure be limited not by this detailed description, but rather by the claims appended hereto. Future filed applications claiming priority to this application may claim the disclosed subject matter in a different manner and may generally include any set of one or more limitations as variously disclosed or otherwise demonstrated herein.

What is claimed is:

1. A non-transitory computer readable medium embodied with programming code executable by a processor, and the processor when executing the programming code is operable to perform functions, including functions to:
   receive a number of blood glucose measurement values over a period of time;
   calculate a correction bolus dosage based on a latest blood glucose measurement value of the number of blood glucose measurement values;
   determine a rate of change of blood glucose values from the number of blood glucose measurement values over the period of time;
   calculate a revised bolus dosage using the determined rate of change of the blood glucose values and the latest blood glucose measurement value;
   apply a function to the correction bolus dosage and the revised bolus dosage, wherein the function outputs a minimum value between the correction bolus dosage and the revised bolus dosage;
   determine a final insulin value based on the output from the function;
   set an insulin bolus dosage using the determined final insulin value; and
   actuate delivery of insulin according to the set insulin bolus dosage.

2. The non-transitory computer readable medium of claim 1, further embodied with programming code executable by the processor, and the processor when executing the programming code is operable to calculate the correction bolus dosage by performing functions to:
   determine a difference between the latest blood glucose measurement value and a target blood glucose value;
   apply an insulin sensitivity factor to the determined difference to provide a personalized insulin value; and
   apply an insulin adjustment factor to the personalized insulin value.

3. The non-transitory computer readable medium of claim 1, further embodied with programming code executable by the processor, and the processor when executing the programming code is operable to calculate the revised bolus dosage by performing functions to:
   access a table of time parameters;
   select a time parameter based on a prediction of a user response time to a dose of insulin, wherein the latest blood glucose measurement value is used in the prediction of the user response time; and
   apply the time parameter to the determined rate of change.

4. The non-transitory computer readable medium of claim 1, further embodied with programming code executable by the processor, and the processor when executing the programming code is operable to calculate the revised bolus dosage by performing functions to:
   determine a rate of change correction factor by multiplying a rate of change by a time parameter;
   modify the latest blood glucose measurement value of the number of blood glucose measurement values using the determined rate of change correction factor;
   determine a difference between the modified latest blood glucose measurement value and a target blood glucose value; and
   apply an insulin sensitivity factor to the determined difference to produce the revised bolus dosage.

5. The non-transitory computer readable medium of claim 1, wherein, when the programming code is executed by the processor, the processor is operable to perform further functions, including functions to:
   determine whether an indication of a meal bolus is to be output, or an indication of a correction bolus is to be output.

6. The non-transitory computer readable medium of claim 5, further embodied with programming code executable by the processor, and the processor when executing the programming code is operable to perform functions, including functions, when applying the function to the correction bolus dosage and the revised bolus, to:
   in response to determining the indication of a meal bolus is to be delivered, retrieve an amount of carbohydrates;
   retrieve an insulin-to-carbohydrates ratio value that is representative of a number of grams of carbohydrates to a number of units of insulin;
   generate a meal parameter using the retrieved amount of carbohydrates and the insulin-to-carbohydrate ratio value;

generate a meal correction bolus dosage by adding the meal parameter to the correction bolus dosage;

generate a meal revised bolus dosage by adding the meal parameter to the revised bolus dosage;

set the meal correction bolus dosage as the correction bolus dosage and set the meal revised bolus dosage as the revised bolus dosage in the function;

reapply the function using the meal correction bolus dosage as a replacement for the correction bolus dosage and the meal revised bolus dosage as a replacement for the revised bolus dosage; and based on the output of the function using the meal correction bolus dosage as the correction bolus and the meal revised bolus dosage as the revised bolus dosage, set a meal bolus dosage as the insulin bolus dosage.

7. The non-transitory computer readable medium of claim 5, further embodied with programming code executable by the processor, and the processor when executing the programming code is operable to perform functions, including functions to:

in response to determining the indication of a correction bolus is to be delivered, actuate the delivery of the insulin.

8. The non-transitory computer readable medium of claim 1, further embodied with programming code executable by the processor, wherein the processor, when receiving the number of blood glucose measurement values is operable to:
receive the number of blood glucose measurement values from a blood glucose monitor via a wireless signal.

9. A device, comprising:

a processor;

a memory storing programming code, an artificial pancreas application, and the memory being operable to store data related to the artificial pancreas application, wherein the programming code and the artificial pancreas application are executable by the processor; and a transceiver operable to receive and transmit signals containing information usable by or generated by the artificial pancreas application, wherein the processor when executing the artificial pancreas application is operable to control delivery of insulin, and to perform functions, including functions to:

obtain a number of blood glucose measurement values;

calculate a correction bolus dosage based on a latest blood glucose measurement value of the number of blood glucose measurement values;

determine a rate of change of blood glucose values from the number of blood glucose measurement values over a period of time;

calculate a revised bolus dosage using the determined rate of change of the blood glucose values and the latest blood glucose measurement value;

apply a function to the correction bolus dosage and the revised bolus dosage, wherein the function outputs a minimum value between the correction bolus dosage and the revised bolus dosage;

determine a final insulin value based on the output from the function;

set an insulin bolus dosage using the determined final insulin value; and actuate delivery of insulin according to the set insulin bolus dosage.

10. The device of claim 9, further comprising:
a pump mechanism operable to be removably coupled to a user; and
a reservoir operable to contain insulin and fluidly coupled to the pump mechanism,
wherein the pump is communicatively coupled to the processor, and is operable to:
expel, in response to an actuation signal from the processor, insulin from the reservoir according to the set insulin bolus dosage.

11. The device of claim 9, wherein the processor when obtaining the number of blood glucose measurement values is operable to:
receive, via the transceiver, signals containing respective blood glucose measurement values of the number of blood glucose measurement values; and
store each of the respective blood glucose measurement values in the memory.

12. The device of claim 9, wherein the processor when actuating delivery of insulin according to the set insulin bolus dosage is operable to:
transmit, via the transceiver, a control signal for receipt by a medical device, wherein the control signal indicates an amount of insulin to be expelled by a medical device.

13. The device of claim 9, further comprising:
a blood glucose sensor communicatively coupled to the processor and operable to measure multiple blood glucose values, wherein the blood glucose sensor provides the number of blood glucose measurement values.

14. The device of claim 9, wherein the processor when calculating the correction bolus dosage is operable to:
determine a difference between the latest blood glucose measurement value and a target blood glucose value;
apply an insulin sensitivity factor to the determined difference to provide a personalized insulin value; and
apply an insulin adjustment factor to the personalized insulin value.

15. The device of claim 9, wherein the processor when calculating the revised bolus dosage is operable to:
access a table of time parameters;
select a time parameter based on a predicted user response time to the latest blood glucose measurement value; and
apply the time parameter to the determined rate of change.

16. The device of claim 9, wherein the processor when calculating the revised bolus dosage is operable to:
modify the latest blood glucose measurement value of the number of blood glucose measurement values using a determined rate of change correction factor, wherein the determined rate of change correction factor is generated from the determined rate of change and a time parameter;
determine a difference between the modified latest blood glucose measurement value and a target blood glucose value; and
apply an insulin sensitivity factor to the determined difference to produce the revised bolus dosage.

17. The device of claim 9, wherein the processor when executing the artificial pancreas application is operable to:
determine whether an indication of a meal bolus or an indication of a correction bolus is to be output;
in response to determining the indication of the meal bolus is to be output, retrieve an amount of carbohydrates;

retrieve an insulin-to-carbohydrates ratio value that is representative of a number of grams of carbohydrates to a number of units of insulin;

generate a meal parameter using the retrieved amount of carbohydrates and the insulin-to-carbohydrate ratio value;

generate a meal correction bolus dosage by adding the meal parameter to the correction bolus dosage;

generate a meal revised bolus dosage by adding the meal parameter to the revised bolus dosage;

reapply the function using the meal correction bolus dosage as a replacement for the correction bolus dosage and the meal revised bolus dosage as a replacement for the revised bolus dosage; and set a meal bolus dosage as the insulin bolus dosage based on the output of the function.

18. The device of claim 9, wherein the processor is operable to obtain the number of blood glucose measurement values from a blood glucose monitor via a wireless signal.

\* \* \* \* \*